US011531650B2

(12) United States Patent
Aronsky et al.

(10) Patent No.: US 11,531,650 B2
(45) Date of Patent: Dec. 20, 2022

(54) COMPUTER-IMPLEMENTED KNOWLEDGE ASSET DISTRIBUTION PLATFORM AND A COMPUTER-IMPLEMENTED METHOD FOR DISTRIBUTING PACKAGES OF KNOWLEDGE ASSETS

(71) Applicant: Semedy AG, Zug (CH)

(72) Inventors: Dominik Aronsky, Rueschlikon (CH); Roberto Rocha, Wellesley, MA (US); Dirk Wenke, Kassel (DE); Saverio Maviglia, Medfield, MA (US)

(73) Assignee: SEMEDY AG, Zug (CH)

( * ) Notice: Subject to any disclaimer, the term of this patent is extended or adjusted under 35 U.S.C. 154(b) by 450 days.

(21) Appl. No.: 16/789,785

(22) Filed: Feb. 13, 2020

(65) Prior Publication Data

US 2021/0255997 A1 Aug. 19, 2021

(51) Int. Cl.
*G06F 16/00* (2019.01)
*G06F 16/182* (2019.01)
*G16H 70/00* (2018.01)
*G16H 15/00* (2018.01)

(52) U.S. Cl.
CPC ......... *G06F 16/1827* (2019.01); *G16H 15/00* (2018.01); *G16H 70/00* (2018.01)

(58) Field of Classification Search
None
See application file for complete search history.

(56) References Cited

U.S. PATENT DOCUMENTS

| 6,550,057 B1* | 4/2003 | Bowman-Amuah ... H04L 67/01 707/999.005 |
| 2005/0228808 A1* | 10/2005 | Mamou ................. G06F 16/254 |
| 2010/0070448 A1* | 3/2010 | Omoigui ............. H01L 27/1463 706/55 |

(Continued)

FOREIGN PATENT DOCUMENTS

CA 2 397 647 A1 8/2001

OTHER PUBLICATIONS

Extended European Search Report dated Jul. 8, 2021 issued in corresponding EP Application No. 21155239.3.

(Continued)

*Primary Examiner* — Farhan M Syed
(74) *Attorney, Agent, or Firm* — Posz Law Group, PLC

(57) ABSTRACT

A computer-implemented knowledge asset distribution platform distributes packages of knowledge assets between plural provider system environments (PSE) and/or consumer system environments (CSE), which store knowledge assets and make the knowledge assets available to users of the CSE. The platform includes one or more processor unit(s), with one or more non-transitory memory unit(s), and a distribution module that distributes packages of knowledge assets. The platform includes a receiver module that receives packages of knowledge assets, a database module that stores packages of knowledge assets and/or stores content information of packages of knowledge assets, a browser module that provides a browser function for browsing the knowledge assets stored by the database module and/or for browsing the content information stored by the database module and a sender module that relays packages of knowledge assets.

23 Claims, 6 Drawing Sheets

(56) References Cited

U.S. PATENT DOCUMENTS

Figure 1:
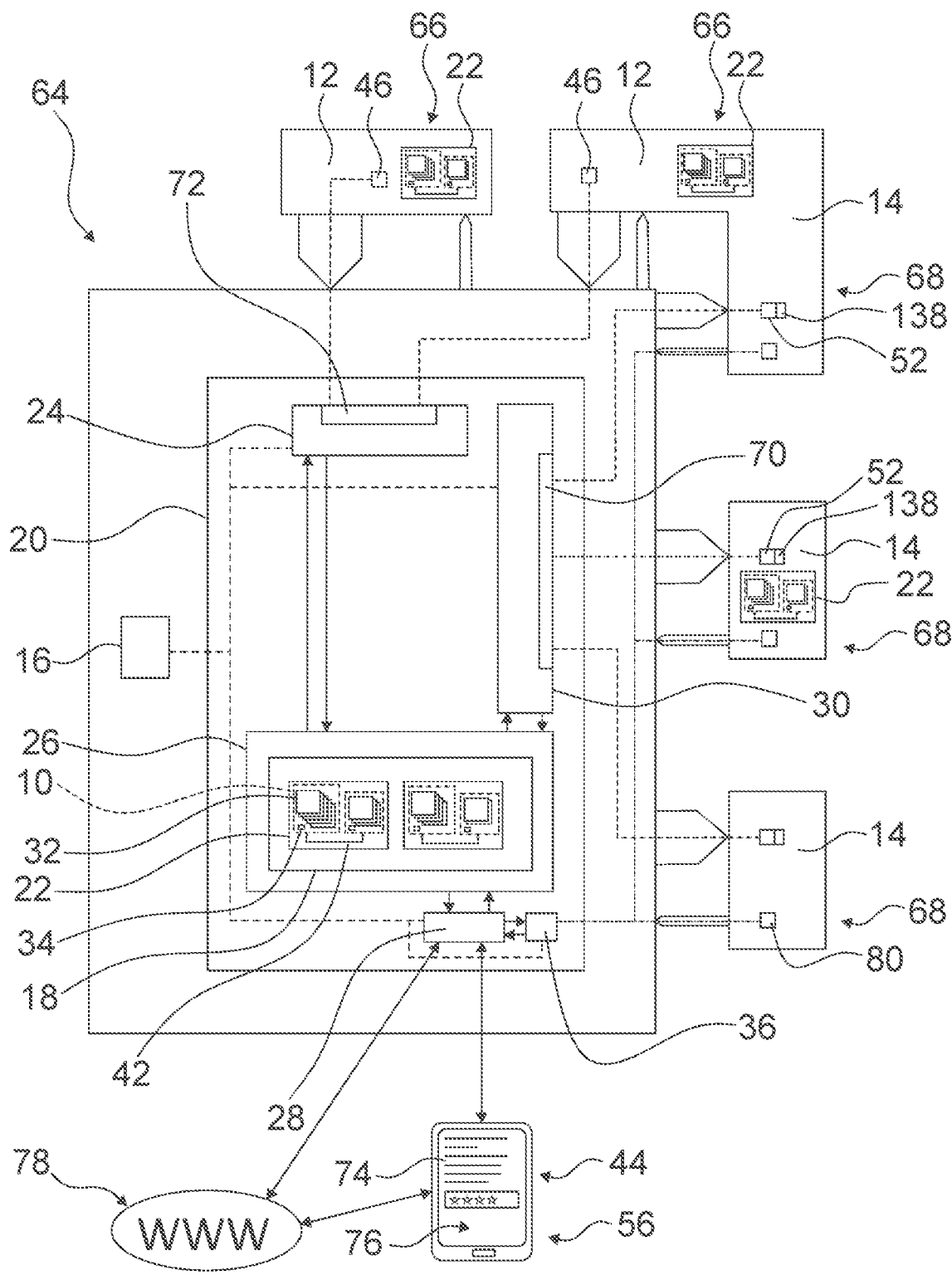

| | | | | |
|---|---|---|---|---|
| 2010/0131874 A1* | 5/2010 | Linthicum | ............. | G16H 40/63 |
| | | | | 715/764 |
| 2010/0138231 A1* | 6/2010 | Linthicum | ............. | G16H 80/00 |
| | | | | 715/764 |
| 2018/0200142 A1* | 7/2018 | Freeman | ................ | G16H 15/00 |

OTHER PUBLICATIONS

"Anonymous" Proxy Server—Wikipedia, Jan. 24, 2020, pp. 1-14, URL:https://en.wikipedia.org/w/index.php?title=Proxy server&oldid=937410931, retrieved on Jun. 23, 2021.
R. Fielding et al., Hypertext Transfer Protocol—HTTP/1.1, RFC2616, Standard Track, The Internet Society, Jun. 1999, pp. 1-176.

* cited by examiner

COMPUTER-IMPLEMENTED KNOWLEDGE ASSET DISTRIBUTION PLATFORM AND A COMPUTER-IMPLEMENTED METHOD FOR DISTRIBUTING PACKAGES OF KNOWLEDGE ASSETS

STATE OF THE ART

The invention relates to a computer-implemented knowledge asset distribution platform and to a computer-implemented method for distributing packages of knowledge assets.

From the state of the art, a wide range of knowledge databases assisting experts of various professions in their daily work are known. Maintaining, customizing and/or keeping up to date such specialized and everchanging knowledge databases is an ambitious and demanding—sometimes tedious—but crucial task.

The objective of the invention is in particular to provide a generic system with advantageous characteristics regarding a targeted distribution of knowledge assets, in particular regarding a sending, a receiving and/or a relaying of packages of knowledge assets between different computer systems. The objective is achieved, according to the invention, by the features of the independent patent claims while advantageous implementations and further developments of the invention may be gathered from the subordinate claims.

Advantages of the Invention

In one aspect of the invention, which may be considered on its own or in combination with at least one further aspect, in particular in combination with one aspect, in particular in combination with any number of the remaining aspects of the invention, a computer-implemented knowledge asset distribution platform, configured to distribute packages of knowledge assets between a plurality of provider system environments (PSE) and/or consumer system environments (CSE), which are configured to at least store knowledge assets and to make the knowledge assets available to users of the CSE, is proposed, with at least one processor unit, with at least one non-transitory memory unit, and with a distribution module which is configured to distribute packages of knowledge assets and comprises a receiver module configured to receive packages of knowledge assets, which packages are configured to be distributed by the knowledge asset distribution platform from at least one PSE and/or to receive content information on the packages of knowledge assets that are to be distributed by the knowledge asset distribution platform from the at least one PSE, a database module configured to store packages of knowledge assets and/or to store content information of packages of knowledge assets, in particular the packages of knowledge assets and/or the content information received by the receiver module, within the non-transitory memory unit, a browser module, in particular a browser and query module, which is configured to provide a browser function for browsing the knowledge assets stored by the database module and/or for browsing and/or finding the content information and/or metadata stored by the database module in order to find and/or locate specific packages of knowledge assets and/or to find and/or locate packages of knowledge assets containing knowledge about specific topics, and a sender module configured to relay packages of knowledge assets, which have for example been selected by a user via the browser module or which for example have been selected by an automated update routine based on an up-to-dateness of the respective packages of knowledge assets, from the non-transitory memory unit and/or from the at least one PSE to at least one CSE, wherein the scope and/or the content of a package of knowledge assets to be distributed via the knowledge asset distribution platform are/is definable by a user of the at least one PSE from a pool of knowledge assets available within the at least one PSE.

In this way advantageous characteristics regarding a data transfer, in particular a targeted distribution of knowledge assets, in particular regarding a sending, a receiving and/or a relaying of packages of knowledge assets between different computer systems, in particular between different PSEs and/or CSEs, are advantageously achievable. In particular, a high degree of customizability of packages of knowledge assets to be distributed may advantageously be provided, thus advantageously allowing a particularly effective usage of network resources, e.g. a bandwidth, a data volume to be transmitted, and/or a particularly high usability of the knowledge asset distribution platform, due to the fact that the knowledge assets of the packages of knowledge assets to be distributed can advantageously be grouped according to freely definable characteristics. Furthermore, an entity which decides to share and/or to provide at least a part of its collection of knowledge assets may advantageously group knowledge assets logically in packages and/or may make a detailed selection regarding which portion of its knowledge assets be made available for distribution.

The knowledge asset distribution platform is in particular implemented as a computer system or at least as part of a computer system, which is preferably included in and/or has access to a large network of computer systems, e.g. an intranet or the Internet. Alternatively, the knowledge asset distribution platform could be implemented at least partly as a virtual server, a distributed computer system and/or as a server which is part of a private or public cloud computing system. The term "to distribute packages of knowledge assets" is in particular to mean at least to receive knowledge assets, to store the received knowledge assets and to send out the stored knowledge assets. A "knowledge asset" is to be understood as a collection of information regarding a specific topic, preferably about a specific object, a specific concept, a specific method, a specific event, a specific condition or similar. For example, a knowledge asset could be information about a specific bio-medical condition, about a specific active ingredient, about a specific medical procedure, etc. A package of knowledge assets contains in particular at least one knowledge asset. Preferably, the package of knowledge assets contains at least a plurality of knowledge assets, which in particular form a collection of knowledge assets which are groupable by at least one common topic. For example, packages of knowledge assets could include at least one plurality of medical and/or bio-medical knowledge assets. The medical and/or bio-medical knowledge assets of a specific package of knowledge assets could for example be grouped by topics like "medications", "symptoms", "treatment instructions", etc. In particular, a package of knowledge assets which is to be distributed by the knowledge asset distribution platform may have at least one dependency by which it can be attributed to at least one further package of knowledge assets. For example, a package of knowledge assets containing mappings between two terminology models, like SNOMED-CT and ICD-10-CM, is attributed with a dependency on two packages of knowledge assets containing the two terminology models, namely in the above example the SNOMED-CT bundle and the ICD-10-CM model. In particular, a distribution of a package of knowledge assets which is attributed with at least one dependency to a target CSE requires either the package of knowledge asset which the distributed package of knowledge assets is dependent on to already be available in the target CSE, or requires a simultaneous distribution of the interdependent packages of knowledge assets to a target CSE. The sender module is in particular configured to verify dependencies of packages of knowledge assets selected for distribution before initiating a send-out protocol and to prevent a transfer of the packages of knowledge assets if a dependent package of knowledge assets is not present in the target CSE or in the selection of packages of knowledge assets to be transferred. It is conceivable that a user, in particular a user of a CSE, can subscribe to the automated update routine, which advantageously automatically selects and relays packages of knowledge assets.

A package of knowledge assets in particular contains at least a schema of a knowledge asset, preferably at least a schema for each knowledge asset of the package of knowledge assets, wherein the same schema may be attributable to more than one knowledge asset. A "schema" of a knowledge asset is in particular, in this context, to be understood as an information about a model which underlies the respective knowledge asset. In particular, the knowledge asset distribution platform may operate a knowledge management system environment (KMSE), which is in particular configured to organize stored knowledge assets. Preferably, the schema of the knowledge asset contains information necessary for integrating the knowledge asset in an existing system environment or in a new system environment that is still to be defined, in particular in a specific KMSE. The KMSE is in particular implemented as a bio-medical KMSE or as a clinical KMSE. Alternatively or additionally, the KMSE may be configured to manage and/or store data which is/are different from bio-medical or clinical data. A "provider system environment (PSE)" is in particular to mean a knowledge database computer system environment which is operated by an entity, e.g. an institution, a hospital, a university etc., intending to provide knowledge assets to be distributed. The provider system environment may be different from a system environment of the knowledge asset distribution platform, in particular from the KMSE of the knowledge asset distribution platform. Preferably, the provider system environment is compatible with the KMSE of the knowledge asset distribution platform. Alternatively or additionally, the knowledge asset distribution platform, in particular the receiver module, may provide an extract-transfer-load functionality (ETL functionality), which is configured to allow an interaction of the knowledge asset distribution platform with PSEs, preferably also with non-compatible PSEs, and in particular allows a handling of knowledge assets or packages of knowledge assets from the non-compatible PSEs for the purpose of integrating the knowledge assets of the non-compatible PSEs in the knowledge asset distribution platform. An operator of a PSE is in particular able to impose restrictions on content which is to be distributed, in particular on packages of knowledge assets, on knowledge assets, in links between knowledge assets and/or on attributes of knowledge assets. Such a restriction could for example be a read-only protection or a prohibition of amendments or changes to at least parts of specific packages of knowledge assets, to at least parts of specific knowledge assets (e.g. a knowledge asset contains at least some unchangeable information), to links between knowledge assets and/or to at least parts of specific attributes of knowledge assets. A "consumer system environment (CSE)" is in particular a knowledge database computer system environment which is run by an entity, e.g. an institution, a hospital, a university etc., intending to consume knowledge assets distributed by the knowledge asset distribution platform, and/or in particular intends to study or to apply the knowledge of the knowledge assets. In particular, the CSE is implemented as a KMSE. In particular, the CSE is compatible with the KMSE of the knowledge asset distribution platform. Alternatively, the CSE operates a knowledge database computer system environment which is different from the KMSE of the knowledge asset distribution platform and/or non-compatible with the KMSE of the knowledge asset distribution platform. The knowledge asset distribution platform, in particular the sender module, may preferably provide an extract-transfer-load (ETL) functionality, which is configured to allow an interaction of the knowledge asset distribution platform with a specific CSE, preferably also with a non-compatible CSE, and in particular allows a distribution of knowledge assets or of packages of knowledge assets to the non-compatible CSE and an integration of the distributed knowledge assets in the non-compatible CSE. The knowledge assets of the distributed packages of knowledge assets are customizable and/or modifiable by the CSE once they have been loaded in the CSE. In particular, it is possible that a CSE is at the same time a PSE or vice versa. In particular, a provider entity of at least one specific package of knowledge assets may at the same time be a consumer entity for at least one further specific set of knowledge assets.

"Configured" is in particular to mean specifically programmed, designed and/or equipped. By an object being configured for a certain function is in particular to be understood that the object fulfills and/or implements said certain function in at least one application state and/or operating state. By a method being "configured" for a purpose is in particular to be understood that the method comprises at least one method step that is specifically directed to the purpose and/or that the method is directly focused on the purpose and/or that the method serves for fulfilling the purpose and is at least partly optimized therefor.

The distribution module is preferably at least partly integrated in the computer system of the knowledge asset distribution platform. In particular, the distribution module may at least partly share hardware of the computer system, e.g. a processor or a memory, with other modules of the knowledge asset distribution platform. Alternatively, the distribution module may be implemented at least partly as a separate server within the computer system of the knowledge asset distribution platform. The distribution module is configured to control and direct data transfer, in particular the distribution of packages of knowledge assets, between the knowledge asset distribution platform, CSEs and/or PSEs. In particular, the distribution module comprises a number of sub-modules which are tasked with different parts of the distribution function of the distribution module. It is conceivable that at least one sub-module of the distribution module, in particular an acquisition module of the receiver module, may at least partly be expanded to external computer systems, e.g. to PSEs and/or CSEs. For example, a provider entity using a non-compatible PSE could employ at least an export function of the ETL functionality of the receiver module, in particular of the acquisition module of the receiver module, to extract knowledge assets from the PSE. In this case the provider entity therefore in particular needs to integrate at least part of the receiver module in the PSE. Alternatively, the receiver module, in particular the acquisition module of the receiver module, could provide a remote database extraction functionality, which is for example configured for extracting knowledge assets from the PSE via a network connection upon receipt of an access permission from the provider entity for an external database access. A "content information" on a package of knowledge assets in particular includes information about the common topic of the package of knowledge assets, information about the provider entity or entities of the package of knowledge assets, information about the most recent update time point of the package of knowledge assets, information about the extent of the package of knowledge assets, e.g. the number of knowledge assets, information about a quality assessment of the content of the package of knowledge assets, etc. A content information about packages of knowledge assets could in particular include information about metadata, for example of the knowledge assets.

The knowledge asset distribution platform, in particular the receiver module, preferably comprises a receiver device, which is in particular configured to receive data packages, e.g. implemented as electric, electromagnetic, acoustic or optical signals, and to interpret the data packages. The database module is preferably at least partly integrated in the computer system of the knowledge asset distribution platform. In particular, the database module may at least partly share hardware of the computer system, e.g. the processor unit or the non-transitory memory unit, with other modules of the knowledge asset distribution platform. The database module comprises in particular at least a read and/or write function, which is configured to control a read and/or write device of the non-transitory memory unit. The receiver module is in particular configured to interact at least with the database module for writing received data into the non-transitory memory unit.

The browser module is preferably at least partly integrated in the computer system of the knowledge asset distribution platform. In particular, the browser module may at least partly share hardware of the computer system, e.g. the processor or the non-transitory memory unit, with other modules of the knowledge asset distribution platform. The browser module is in particular configured to at least interact with the database module in order for reading data out of the non-transitory memory unit. In particular, the browser module further provides a search function, which is configured for searching the knowledge assets stored by the database module and/or for searching the content information stored by the database module in order to find and/or locate specific packages of knowledge assets and/or to find and/or locate packages of knowledge assets containing knowledge about specific topics. In particular, the browser module further provides a visualization function, which is configured for a visualization of content of at least one package of knowledge assets and/or for a visualization of the results of a search performed by the search function. In particular, the visualization function is configured for a transmission of a display signal to a display device of the knowledge asset distribution platform or to an external display device which is connected with the knowledge asset distribution platform.

The knowledge asset distribution platform, in particular the sender module, in particular comprises a sender device, which is in particular configured to send out data packages, e.g. implemented as electric, electromagnetic, acoustic or optical signals, which are to be received by CSEs. The sender module is preferably at least partly integrated in the computer system of the knowledge asset distribution platform. In particular, the sender module may at least partly share hardware of the computer system, e.g. the processor unit or the non-transitory memory unit, with other modules of the knowledge asset distribution platform. The sender module is in particular configured to interact at least with the database module for a reading of stored data out of the non-transitory memory unit and for a transmission of the data via the sender device. In particular, it is conceivable that the scope or the content of a package of knowledge assets to be distributed is definable at least semi-automatically by the receiver module, in particular by the export function of the ETL functionality of the receiver module, during an export of knowledge assets from a PSE. In particular, the receiver module, preferably the export function of the ETL functionality of the receiver module, comprises an inference unit, in particular an inference engine, and/or is configured to employ an inference unit of the knowledge asset distribution platform. The inference unit is configured to analyze at least the content of knowledge assets and/or the metadata of knowledge assets in order to determine scopes and/or contents of packages of knowledge assets from an entirety of knowledge assets available within a PSE, thereby forming logical groupings of knowledge assets. For example, the receiver module uses the inference unit to at least semi-automatically determine knowledge assets of a PSE which fit a specific scope, e.g. the knowledge assets which concern medications or a specific type or class of disease, e.g. cancer, and groups them in a package of knowledge assets. The term "semi-automatically" is in particular to mean, in this context, in such a way that, while an attribution of a knowledge asset to a package of knowledge assets of a specific group is performed automatically, for at least a fraction of the attributed knowledge assets a confirmation and/or a validation by a user may be requested by the inference unit. Preferably the grouping of knowledge assets by the receiver module during an export of knowledge packages from a PSE is fully automatized. In particular, each package of knowledge assets which is received by the receiver module or which is sent out by the sender module has a unique identifier, e.g. including a revision number or a receiving/sending date, in order to allow a rapid and simple identification and/or correlation of each package of knowledge assets distributed by the knowledge asset distribution platform. Furthermore, it is conceivable that a package of knowledge assets or even an individual knowledge asset of a package of knowledge assets has an identifier, which defines a mandatory or an optional connection of the package of knowledge assets or the individual knowledge asset of a package of knowledge assets with at least one further package of knowledge assets of at least one further individual knowledge asset of a package of knowledge assets.

Moreover, it is proposed that the package of knowledge assets comprises at least one instance of a knowledge asset, preferably a plurality of interlinked instances of knowledge assets, and at least one schema of at least one knowledge asset, which is in particular attributed to at least one instance of a knowledge asset of the package of knowledge assets, preferably to a plurality of interlinked instances of knowledge assets of the package of knowledge assets. Thus, an integration in an existing CSE, in particular in a KMSE, may advantageously be simplified. In particular, a compatibility between the packages of knowledge assets to be distributed and the receiving CSE may advantageously be increased. Furthermore, this advantageously allows a receiving entity of a distributed package of knowledge assets to decide whether it wants to implement the pure knowledge data, the underlying model or both. The plurality of interlinked knowledge assets in particular comprises knowledge assets which refer to each other via pointers.

Furthermore, it is proposed that the distribution module comprises a tracker module, which is configured to monitor an up-to-dateness of a package of knowledge assets which has been relayed, in particular distributed, to at least one CSE via the sender module. Thus, a high-level up-to-dateness of a distributed package of knowledge assets is advantageously achievable and/or guaranteeable, which in turn advantageously provides a high degree of reliability for the consumer. Furthermore, a high degree of usability of the knowledge asset distribution platform is advantageously ensured, in particular due to the fact that a user effort necessary to keep a knowledge database or a KMSE up-to-date is considerably reducible. The tracker module is preferably at least partly integrated in the computer system of the knowledge asset distribution platform. In particular, the tracker module may at least partly share hardware of the computer system, e.g. the processor or the non-transitory memory unit, with other modules of the knowledge asset distribution platform. In particular, the tracker module is configured to create and store a momentary image of a package of knowledge assets at the point in time it is relayed to a specific CSE. In particular, the tracker module is configured to routinely compare a current state of the package of knowledge assets to a previous state of the package of knowledge assets, in particular to the image of the package of knowledge assets, to determine a difference, in particular to determine an up-to-dateness of the package of knowledge assets that corresponds to the image of the package of knowledge assets. In particular, a "state of a package of knowledge assets" is to be understood, in this context, as at least a fraction of the content, preferably the complete content, of the knowledge assets of a package of knowledge assets and/or at least one metadata, preferably at least a plurality of metadata, of at least one knowledge asset of the package of knowledge assets, of at least a plurality of knowledge assets of the package of knowledge assets or of the package of knowledge assets. In particular, the tracker module is configured to monitor the up-to-dateness of all packages of knowledge assets previously relayed by the sender module individually.

Additionally, it is proposed that the tracker module is configured to send out an update signal, in particular an update notification, to the CSE, in particular to a user of the CSE, when a relevance indicator of a package of knowledge assets reaches or surpasses a predetermined condition. Thus, a high-level up-to-dateness of a distributed package of knowledge assets is advantageously achievable and/or guaranteeable, which in turn advantageously provides a high degree of reliability for the consumer. Furthermore, a high level of usability of the knowledge asset distribution platform is advantageously ensured, in particular due to the fact that a user effort necessary to keep a knowledge database or a KMSE up-to-date is considerably reducible. The tracker module is in particular configured to interact at least with the sender module for a transmission of the update signal and/or of the update notification via the sender device. Preferably the update signal, in particular the update notification, is sent to the user of the CSE as an electronic message, for example as a text message like an email, a chat message, a messenger notification or similar, as an acoustic signal, for example a warning sound or a voice message or similar, or as a visual message, for example an illumination of a signal lamp or a change of color of a user interface or similar. In particular, the update signal contains information about the up-to-dateness of the package of knowledge assets in question, e.g. about the number of changed knowledge assets, about the time elapsed since a preceding update, about the type of changed content or metadata of the package of knowledge assets or similar. In addition, it is conceivable that the update signal contains a recommendation regarding the urgency of an update, which may in particular depend on the type of changed content or on the amount of changed content. For example, the urgency of an update is higher due to changes concerning the message of a knowledge asset, e.g. a change in a dosage recommendation of a medication, an issuance of an FDA warning or a procedural change in a diagnosis scheme, than due to changes concerning formalities related to a knowledge asset, e.g. a change of name of a producing company of a medication or an update of a list of reference literature attached to a knowledge asset. Furthermore, the urgency of an update is, for example high if the tracker module detects a revision of a large set of knowledge assets within the package of knowledge assets in contrast to a revision of only one single knowledge asset. Additionally, the urgency of an update is, for example, high if at least one knowledge asset has been revised more than once since the preceding update in contrast to only a single revision of a knowledge asset. Moreover, the urgency of an update is, for example, higher if a knowledge asset is completely retired, i.e. the knowledge asset is deactivated and no new revision of the knowledge asset exists than if a knowledge asset is merely replaced by a revised version. A "relevance indicator" is in particular to mean an update signal which could, for example, be implemented as a threshold, as a time elapsed since a previous update, as a date, like an expiry date, as an indication of a nature, in particular a criticality, of a change. The relevance indicator is in particular customizable and/or adaptable by a consumer and/or by a provider of a particular package of knowledge assets. In particular, a determination of the relevance indicator can be restricted to a fraction of the knowledge assets of a package of knowledge assets. For example, a user, in particular a consumer, who is only interested in an up-to-dateness of a subset of the knowledge assets of a package of knowledge assets, e.g. only in knowledge assets related to a specific medical condition like cancer or bone fractures, or only in knowledge assets related to a specific field of knowledge like pediatrics or gynecology or only in knowledge assets relevant for a specific profession, like for pediatric nurses or geriatric nurses, could advantageously restrict the determination of the relevance indicator to this subset. In particular, changes of other knowledge assets within the packages of knowledge assets of this user accordingly contribute to a decision if an update signal or an update notification is sent out by the tracker module.

Also, it is proposed that the relevance indicator of the package of knowledge assets is implemented as a relevance parameter, which is determined by the tracker module for a package of knowledge assets upon an update of at least one knowledge asset of the package of knowledge assets and/or upon a creation or deletion of at least one new knowledge asset, and which is established by the tracker module at least in part based at least on a weighting and/or a judging of a type or an extent of a detected change at least of the at least one updated knowledge asset of the package of knowledge, in particular of a combination of all updated knowledge assets of the package of knowledge assets, wherein the predetermined condition is a set of alert conditions corresponding to particular relevance parameter definitions, e.g. a minimal relevance parameter value determined for a change of a single knowledge asset and/or for a combined change of all knowledge assets or for an occurrence of at least one particular alert state. Thus, a sending out of update signals can advantageously be optimized, in particular as the system is capable of making a pre-selection regarding which updates of distributed packages of knowledge assets require an immediate or timely update to maintain a sufficient degree of reliability and applicability and which updates of distributed packages of knowledge assets are less time-critical. This advantageously allows achieving a high usability of the knowledge asset distribution platform, in particular by avoiding an overwhelming of a user due to a high frequency of updates. Furthermore, a size of a data volume to be transferred is advantageously minimizable, advantageously saving network bandwidth and costs involved. In particular, the relevance parameter is implemented as a numeric value, as a string or as an on/off status. It is conceivable that the tracker module calculates the relevance parameter based on an extent of a change of a knowledge asset or a combination of knowledge assets, on a type or nature of a change of a knowledge asset or a combination of knowledge assets, or on a point in time, e.g. a date, of a change of a knowledge asset or a combination of knowledge assets. In particular, some information entries, preferably each information entry, of a knowledge asset are attributed with a certain criticality marker, which may be employed for the determination of the relevance parameter. The criticality marker could be for example a criticality value or a simple "note" whether a specific information entry is critical or not. The criticality markers could in particular be staged. In this way a gradation could advantageously be achieved, according to which even a single very critical change or only a number of less critical changes could entail an update signal. The criticality markers may in particular be added at least partially by a creator of a content, in particular the provider of the package of knowledge assets, and/or may be calculated by the tracker device on the basis of the available knowledge assets or the available metadata, in particular in a semi-automatic or a fully automatized way. By "establishing the relevance parameter based at least on a weighting" is in particular to be understood that the tracker module is configured to apply a weight to a detected change for categorizing its importance. By "establishing the relevance parameter based at least on a judging" is in particular to be understood that the tracker module is configured to judge, in particular with regard to set user preferences, whether a detected change is sufficiently relevant to trigger an update signal. In particular, a "type of change" comprises in this context a form change, a change of a reference, a change of a category, a change of metadata, a change of text content or similar. In particular, an "extent of a change" is to mean, in this context, a fraction of a total information of a knowledge asset which is changed or a criticality of the information of a knowledge asset which is changed. A "predetermined condition" is in particular to mean, in this context, a condition which is an underlying condition of a model or a schema associated with a CSE or a KMSE or a customizable condition set by a user of the CSE or of the KMSE. In particular, "relevance parameter definitions" are in this context to mean a set of relevance parameters which trigger an update signal once the tracker module registers that they are met or reached. Additionally or alternatively, it is also conceivable that the relevance parameter is determined by the tracker module for a package of knowledge assets upon a creation or upon a deletion of at least one new knowledge asset and that the relevance parameter is established by the tracker module at least in part based at least on a weighting and/or a judging of a newly added or deleted knowledge asset of the package of knowledge assets.

Furthermore, it is proposed that the relevance indicator of the package of knowledge assets is a percentage of knowledge assets which have changed since a preceding transmission of the package of knowledge assets to a respective CSE, wherein the predetermined condition is a threshold, in particular a maximum percentage of knowledge assets which have changed since a preceding transmission of the package of knowledge assets to a respective CSE. Thus, a sending out of update signals is advantageously optimizable, in particular by keeping a number of update invitations at a manageable level. Thereby, a high degree of usability of the knowledge asset distribution platform is advantageously achievable, in particular as an overwhelming of a user is avoided by a high frequency of updates. Furthermore, an amount of a data volume to be transferred is advantageously minimizable, thus advantageously saving network bandwidth and costs involved. In particular, the maximum percentage is at least 0.5%, preferably at least 1%, advantageously at least 3%, preferentially at least 5% and particularly preferentially at least 10%. Additionally or alternatively, it is also conceivable that the relevance indicator, in particular the percentage value of the relevance indicator, includes the knowledge assets which have been deleted from a package of knowledge assets and/or which have been added to a package of knowledge assets since a preceding transmission of the package of knowledge assets to a respective CSE and that in this case the predetermined condition is a maximum percentage of all knowledge assets which have changed, which have been deleted and/or which have been added since a preceding transmission of the package of knowledge assets to the respective CSE.

Moreover, it is proposed that the tracker module is configured to relay an updated version of a previously relayed and now out-of-date package of knowledge assets to a CSE, in particular via the sender module, and that the tracker module is configured to detect modifications of knowledge assets within the package of knowledge assets to be updated and/or modifications of links between knowledge assets within the package of knowledge assets to be updated, which were introduced on the side of the CSE. Thus, it is advantageously achievable that customizations and/or localizations made by a user, in particular by a consumer, of a distributed package of knowledge assets on at least some of the knowledge assets of the distributed package of knowledge assets are retained in the wake of an update, thereby advantageously avoiding an undesired loss of customization and/or localization. A "modification of a knowledge asset introduced on the side of the CSE" is in particular to mean a customization and/or a localization of a content or a metadata of a knowledge asset or of a schema of the knowledge asset, in particular the CSE. In particular, the tracker module may at least partly be expandable to external computer systems, e.g. to PSEs and/or CSEs, in particular allowing it to effectively track custom modifications of knowledge assets of the CSE. It is conceivable that different instances of knowledge assets and/or different versions of knowledge assets are simultaneously active, in particular within a CSE and/or within a PSE. Furthermore, it is conceivable that different instances of knowledge assets and/or different versions of knowledge assets are simultaneously distributed by the knowledge asset distribution platform. This could be the case, for example, if different instances of knowledge assets and/or different versions of knowledge assets are used or linked to by different packages of knowledge assets available on a CSE, a PSE and/or the knowledge asset distribution platform.

In addition, it is proposed that the tracker module is configured to prompt the user for confirmation, in particular by a query, before a knowledge asset with a detected modification is overwritten and/or replaced. Thus, it is advantageously achievable that, if desired, customizations and/or localizations made by a user, in particular by a consumer, of a distributed package of knowledge assets on at least some of the knowledge assets of the distributed package of knowledge assets are retained during an update. In particular, a user-reviewed selection regarding which customizations/localizations to keep and which customizations/localizations to overwrite or replace may advantageously be facilitated. In particular, the query contains a checkback whether a specific knowledge asset should be overwritten or replaced by the update or not. In particular, the prompting of the query can be requested by a user of the knowledge asset distribution platform. Preferably conditions defining in which instances a detected modification leads to a prompting of the query are adaptable. It is conceivable that specific knowledge assets can be attributed with flags, which either lead to a prompting of the query, avoid the prompting of the query, allow an overwriting or replacing of the knowledge asset independently from the detected modification, in particular without prompting a query, or prohibit an overwriting or replacing of the knowledge asset at all times, in particular without prompting a query. The query is particularly intended as part of a semi-automatic or supervised update process.

Moreover, it is proposed that in case a customization and/or a localization of knowledge assets within the package of knowledge assets or of packages of knowledge assets is detected by the tracker module, the customization and/or a localization is at least partly, preferably entirely, retained after the update. Thus, customizations and/or localizations made by a user, in particular by a consumer, can advantageously be protected and/or guaranteed. In particular, in case a customization and/or a localization of knowledge assets within the package of knowledge assets or of packages of knowledge assets is detected by the tracker module, the tracker module prevents the customized and/or a localized knowledge assets and/or packages of knowledge assets from being overwritten.

Besides, it is proposed that the computer-implemented knowledge asset distribution platform comprises an interface module, which is configured to allow remote access to packages of knowledge assets distributed by the distribution module, in particular via a web browser, via a web-service or via another distribution method. This advantageously allows improving an accessibility of packages of knowledge assets for a consumer, in particular by facilitating a remote access independently from the CSE. The interface module is in particular implemented as a cloud-based interface module, preferably as a Software-as-a-service (Saas) interface module or similar. In particular, a consumer is enabled to access, via the interface module, packages of knowledge assets which he has previously requested access to. In particular, the interface module is implemented as a computer system or at least as part of a computer system, which is preferably accessible via an intranet or the Internet. Alternatively, the interface module could at least partly be implemented as a virtual server, a distributed computer system and/or as a server which is part of a private or public cloud computing system. The interface module in particular operates a KMSE in order to organize and display the knowledge assets available on the knowledge asset distribution platform. By using the interface module, a consumer is in particular granted access to the KMSE. In particular, an access via the interface module, i.e. an access to the knowledge assets of the KMSE of the interface module, may optionally be limited and/or restricted in any degree.

Furthermore, it is proposed that the receiver module comprises the acquisition module, which is configured to acquire at least a portion of knowledge assets of the PSE, thereby defining a package of knowledge assets, wherein the non-transitory memory unit comprises instructions that, when performed by the processor unit, make the acquisition module identify knowledge assets belonging to the portion of knowledge assets which are to be acquired from the PSE by the acquisition module, including all links and attributes, e.g. metadata, connected with the knowledge assets of said portion of knowledge assets, identify all links connecting knowledge assets of said identified portion with knowledge assets of the PSE outside the identified portion of knowledge assets, create an, in particular virtual, copy of said identified portion of knowledge assets from the PSE, tag the identified links of said, in particular virtual, copy of the portion of knowledge assets as at least semi-broken links, i.e. in particular as weak links, and render the copy of knowledge assets from the PSE, including all intact links, preferably strong links and/or established links, between knowledge assets and including the weak links, available for access via the knowledge asset distribution platform, in particular for a subsequent relaying to a CSE via the sender module. Thus, a compatible export format of packages of knowledge assets is advantageously achievable, in particular due to avoiding any broken or corrupt links within the package of knowledge assets, which could be irretrievable in a reconciliation process of the package of knowledge assets with a CSE, in particular a receiving KMSE. This advantageously facilitates an effective and in particular at least semi-automatic transfer of packages of knowledge assets between KMSEs, in particular between different or even not mutually compatible KMSEs, preferably CSEs and/or PSEs. Consequently, a high degree of usability is advantageously achievable.

Additionally, a high degree of interoperability between different knowledge databases, in particular between different KMSEs, is advantageously achievable. Therefore, resource requirements, in particular for labor resources or for computing resources, are advantageously be reducible. An intact link or a (successfully) established link is preferably to be identified as a strong link. A weak link, which becomes closed and/or connected, in particular re-connected, preferably becomes a strong link and, in particular, is no longer to be identified as a weak link.

The acquisition module is preferably at least partly integrated in the computer system of the knowledge asset distribution platform and/or the receiver module. In particular, the acquisition module may at least partly share hardware of the computer system, e.g. the processor or the memory, with other modules of the knowledge asset distribution platform, in particular with the receiver module. Alternatively, the acquisition module may at least partly be implemented as a separate server within the computer system of the knowledge asset distribution platform or may be implemented at least partly, in particular completely, external to the computer system of the knowledge asset distribution platform. In particular, the knowledge asset distribution platform may offer a downloadable software package allowing a user an establishing or a creation of an external acquisition module, which is completely on the side of the PSE, e.g. operated by a computer system which is part of the PSE or closely linked to the PSE. A "weak link" or an "at least semi-broken link" is in particular a link, e.g. between two knowledge assets, which is unlinked during an export procedure, e.g. because only one of the two knowledge assets is included in the package of knowledge assets which is to be exported, and subsequently is tagged or flagged by the acquisition module with a weak link tag. The weak link tag is in particular implemented as a computable and/or machine-interpretable tag. Preferably the weak link tag is implemented as a human-readable tag or at least the weak link is transformable in human-readable information. The weak link tag is at least accompanied by, in particular computable and/or machine-interpretable, preferably human-readable, instructions and/or information, which are intended to at least describe at least a preferred target of the corresponding weak link and/or at least a list of possible targets of the corresponding weak link. Preferably the weak link tag contains the, in particular computable and/or machine-interpretable, preferably human-readable, instructions and/or information which are intended to at least describe or identify at least the preferred target of the corresponding weak link and/or at least the list of possible targets of the corresponding weak link. In particular, the list of targets may include only one specific target. The computable and/or machine-interpretable information and/or instructions could in particular be implemented as at least one code, as at least one checksum, as at least one hash or similar. The "target" of the weak link is in particular to be understood as the knowledge asset which contains at least part of the information, preferably the full information contained in a knowledge asset previously pointed at by the link. In particular, the term "rendering an item available for access via the knowledge asset distribution platform" is to mean that the item which was prepared and/or downloaded from the PSE implemented as a detached item, in particular a detached package of knowledge assets, is subsequently stored within the non-transitory memory unit of the knowledge asset distribution platform, in particular making the item browsable or findable by the browser module, and preferably making the item usable or downloadable by a consumer accessing the knowledge asset distribution platform. In particular, a definition of the content of the package of knowledge assets, i.e. the knowledge assets grouped in the package of knowledge assets which are to be acquired by the acquisition module, is performed in a manual selection by a user of the PSE selecting at least a fraction of the knowledge assets to be included in the package of knowledge assets. Preferably, the definition of the content of the package of knowledge assets is performed at least semi-automatically or automatically. For example, in a semi-automatic content definition, the acquisition module could make suggestions as to which additional knowledge assets could logically be included, based on already selected knowledge assets, and/or the acquisition module may make suggestions as to which knowledge assets could logically be grouped together under specific topics, which in particular need to be confirmed or rejected by a user of the PSE. For example, in an automatic content definition, the acquisition module could decide on which knowledge assets could logically be grouped together under specific topics, which in particular need to be confirmed or rejected by a user of the PSE. A user could, for example, instruct the acquisition module to group knowledge assets dealing with gerontologic topics in a package of knowledge assets and/or to group knowledge assets dealing with pediatric topics in a further package of knowledge assets. An open link or a broken link, in particular a semi-broken, is preferably to be identified as a weak link.

Moreover, it is proposed that the sender module comprises a consumer import module, which is configured to import a package of knowledge assets to a CSE, thereby integrating the imported package of knowledge assets in an existing set of knowledge assets of the CSE, and with the non-transitory memory unit comprising instructions that, when performed by the processor unit, make the consumer import module copy the package of knowledge assets to a database of the CSE, identify all weak links connecting knowledge assets of the package of knowledge assets to be imported with target knowledge assets outside said package of knowledge assets, for example by searching for weak link tags, in particular read, interpret and/or analyze the weak link tags of the identified weak links, search at least semi-automatically, preferably automatically, for knowledge assets in the CSE which correspond to said target knowledge assets, and connect at least a portion of the weak links by, in particular automatically, preferably semi-automatically, establishing links, preferably strong links, connecting the respective knowledge assets of the package of knowledge assets to said corresponding target knowledge assets. Thus, a high degree of usability may advantageously be reached. Furthermore, an integration of an imported package of knowledge assets can advantageously be facilitated, thereby advantageously reducing a time requirement and/or a workload for an operator of a CSE.

The consumer import module is preferably at least partly integrated in the computer system of the knowledge asset distribution platform and/or the receiver module. In particular, the consumer import module may at least partly share hardware of the computer system, e.g. the processor or the memory, with other modules of the knowledge asset distribution platform, in particular with the receiver module. Alternatively, the consumer import module may at least partly be implemented as a separate server within the computer system of the knowledge asset distribution platform or may be implemented at least partly, in particular completely, external to the computer system of the knowledge asset distribution platform. In particular, the knowledge asset distribution platform may offer a downloadable software package allowing a user an establishing or a creation of an external consumer import module, which is completely on the side of the CSE, e.g. operated by a computer system which is part of the CSE or closely linked to the CSE. In particular, a knowledge asset "corresponds to a target knowledge asset" if the content of the knowledge asset matches, at least for a bigger part, the content of a knowledge asset from the PSE which the knowledge asset has previously been linked to and or the required content indicated by the weak link tag. The term "for a bigger part" is to mean, in this context by 66%, preferably by 75%, advantageously by 85% or favorably by 95%.

In a further preferred embodiment of the knowledge asset distribution platform it is proposed that the consumer import module comprises a linkage unit, which is configured to guide a user in an at least semi-automatic way through a linkage process for a connection and/or a removal of weak links during an import of a package of knowledge assets. Thus, a high degree of usability is advantageously achievable, in particular due to a reduction of a time requirement and a workload necessary to consolidate a newly imported package of knowledge assets in the CSE. Furthermore, erroneous linkages are advantageously avoidable, which in particular leads to a high degree of safety and reliability of the resulting CSE databases. Additionally, a functionality of the CSE may advantageously be ensured by an absence of weak, potentially corrupt, links. For example, a semantic engine of the CSE, in particular of a browser module of the CSE may be incapable of handling weak links and an optimal functionality of the semantic engine may be ensured by re-connecting or removing the weak links. In particular, the linkage process depends on the content and the type of the knowledge asset (for example, knowledge assets using unique identifiers such as Life Science Identifiers (LSIDs) and knowledge assets without unique identifiers require different linkage schemata and processes) and/or on the type and the structure of the CSE in the importing side (for example, a CSE using a KMSE which is related to the KMSE of the knowledge asset distribution platform also requires a different linkage schema and process). In particular, the knowledge asset distribution platform may comprise a variety of downloadable software packages allowing a user the establishing or the creation of external consumer import modules, which are completely on the side of the respective CSE and which are tailored for the specific features, e.g. a data structure, etc., of this respective CSE. A "removal of a weak link" is in particular to mean an inactivation of the corresponding link and/or a tagging and/or flagging of the corresponding link with an exceptional value, in particular a value which is interpretable by a semantic engine.

In addition it is proposed that the linkage unit is configured to search the existing knowledge assets of the CSE, to compare at least one characteristic of the existing knowledge assets of the CSE, in particular at least one computable and/or machine-readable information and/or instruction, preferably a code, a hash or a checksum, to at least one characteristic of a weak link, in particular to at least one information of a weak link tag, in particular to either automatically resolve and/or re-connect the weak link or to create a list of probable target knowledge assets for the weak link on the basis of the existing knowledge assets of the CSE and to display the list of probable target knowledge assets to a user for selection, in particular by a display device of the CSE. In particular, a user selection leads to a resolving and/or re-connecting of the weak link by connecting the target knowledge asset comprising the weak link with the target knowledge asset selected by the user. Thus, a high degree of usability is advantageously achievable, in particular due to a reduction of a time requirement and a workload necessary to consolidate a newly imported package of knowledge assets in the CSE. Furthermore, erroneous linkages are advantageously avoidable, which in particular results in a high degree of safety and reliability of the resulting CSE databases. It is conceivable that, in case a target knowledge asset is identified with a high degree of correspondence, the automatic resolving and/or re-connecting of the weak link is executed while at a lower degree of correspondence the user-assisted resolving and/or re-connecting using the list of probable target knowledge assets is executed. A "high degree of correspondence" is in particular to mean, in this context, a correspondence by at least 90%, preferably by at least 95% or preferentially by 100%. A "lower degree of correspondence" is in particular to mean, in this context, a correspondence by less than 100%, preferably by less than 95% or preferentially by less than 90%. A "resolving" of a weak link is in particular to mean a re-connection, an inactivation or a removal of a weak link.

It is further proposed that, in case a weak link of a knowledge asset is not re-connected during the import, e.g. by a user selection, the linkage unit inserts an exceptional value in the knowledge asset, indicating that it has not been possible to establish a connection of the weak link. Thus, a functionality of the CSE may be advantageously ensured by an absence of weak, potentially corrupt, links. For example, a semantic engine of the CSE, in particular of a browser module of the CSE, may be incapable of handling weak links and an optimal functionality of the semantic engine, which in particular ignores entries with exceptional values, may be ensured by inserting exceptional values in the formerly weak links.

Moreover, it is proposed that the linkage unit, before inserting the exceptional value in the knowledge asset, reviews an integrity of the knowledge asset by reassessing compliance with at least one integrity constraint, in particular at least one semantic integrity constraint and/or at least one structural integrity constraint, like a cardinality of a knowledge asset, which is in particular set by the respective CSE and advantageously prevents an insertion of the exceptional value if the integrity constraint would be violated by the insertion of the exceptional value. Thus, a functionality of the CSE including the newly imported package of knowledge assets may be advantageously ensured. Preferably the semantic integrity constraint and/or the structural integrity constraint are/is customizable and/or extendable. Examples for semantic integrity constraints and/or structural integrity constraints could be that a) cardinalities must be satisfied, b) relation values must satisfy range restrictions, c) attribute values must comply with the defined datatype or d) when defined, values must satisfy declared pattern restrictions, etc.

Furthermore, it is proposed that upon a detection of a violation of an integrity constraint by the linkage unit, the consumer import module transitions from an automatic import mode in an at least semi-automatic import mode and sends out a notification, in particular to a user of the CSE, requesting user guidance, and/or to the browser module. Thus, a high degree of usability is advantageously achievable, in particular due to a reduction of a time requirement and a workload necessary to consolidate a newly imported package of knowledge assets in the CSE. Furthermore, erroneous linkages are advantageously avoidable, which in particular leads to a high degree of safety and reliability of the resulting CSE database. The notification is in particular sent via a communication device, like a mobile phone or similar, and/or directly via the CSE and/or via the knowledge asset distribution platform.

Additionally it is proposed that upon receiving the notification, the browser module initiates a search for at least one knowledge package which, in particular in a combination with the package of knowledge assets to be imported to the CSE and/or the knowledge assets already available in the CSE, is suited to at least partially resolve the violation of the integrity constraint, wherein the browser module transmits a notification to the user of the CSE suggesting required knowledge packages or knowledge assets. Thus, a high degree of usability is advantageously achievable, in particular due to a reduction of a time requirement and a workload necessary to consolidate a newly imported package of knowledge assets in the CSE by facilitating an identification and/or a locating of complementary or obligatory additional knowledge packages. In particular, the "knowledge package" comprises a package of knowledge assets which is different from the package of knowledge assets to be imported to the CSE and/or from the packages of knowledge assets already available in the CSE or a knowledge source external to the knowledge asset distribution platform providing knowledge assets or packages of knowledge assets. In particular, the browser module is configured to search an internal database within the at least one non-transitory memory unit of the knowledge asset distribution platform, to search a list of externally available packages of knowledge assets, which is stored within the at least one non-transitory memory unit of the knowledge asset distribution platform and/or to search external resources via a network connection in order to find suitable complementary or obligatory knowledge packages or knowledge assets.

In addition it is proposed that the browser module is configured to create and prepare for display, in particular on a display device associated with the knowledge asset distribution platform, at least one ranked list of related packages of knowledge assets which are to be distributed via the knowledge asset distribution platform, wherein a rank of the ranked list depends on and/or is computed based on a total number of weak links which are potentially re-connectable by a combination of the package of knowledge assets with the respective related package of knowledge assets. Thus, a high degree of usability, a high degree of lucidity and/or a high degree of organization of a knowledge database are/is advantageously achievable. In particular, the computation of the ranked list considers knowledge assets or packages of knowledge assets already available in a respective CSE. Preferably the computation of the ranked list further considers other locally available items containing suitable information or content that is potentially capable of closing at least one of the weak links of a package of knowledge assets which is to be distributed. In particular, the browser module is configured to query the respective CSE in order to determine a content and/or knowledge assets, in particular the versions and/or instances of the knowledge assets, already available in the CSE, and/or to receive information about the content and/or knowledge assets, in particular the versions and/or instances of the knowledge assets, already available in the CSE, via a network data connection. In particular, the browser module is configured to query the respective CSE in order to determine a computing infrastructure and/or a type of KMSE and/or to receive information about the computing infrastructure and/or the type of KMSE via the network data connection. In particular, the suggested packages of knowledge assets of the ranked list are arranged in a descending order by a number of weak links of a selected package of knowledge assets that are potentially re-connectable by the suggested packages of knowledge assets, wherein the suggested packages of knowledge assets comprise all packages of knowledge assets available via the knowledge asset distribution platform. Preferably the suggested packages of knowledge assets of the ranked list are arranged in a descending order by the number of weak links of the package of knowledge assets which remain after a successful integration of the package of knowledge assets in a specific CSE, in particular omitting all weak links which are already re-connected during integration of the package of knowledge assets in the specific CSE. It is conceivable that further parameters are considered for the computation of the ranked list. In particular, a further parameter is implemented as a quality parameter conveying information about a quality of a content or a scope of a respective package of knowledge assets. The quality parameter in particular comprises a validity parameter, which may in particular be based on an expert opinion or on a collection of user opinions about a specific package of knowledge assets, an applicability parameter, which in particular may be based on an expert opinion or on a collection of user opinions about a specific package of knowledge assets, and/or a reputation parameter, which is based on a reputation of a provider entity of a specific package of knowledge assets, e.g. a renowned medical institute or a renowned hospital may be attributed with a particularly positive reputation parameter. In particular, another further parameter is implemented as an up-to-dateness parameter conveying information about the most recent update of the package of knowledge assets, e.g. a time elapsed since the most recent update of the package of knowledge assets.

Moreover, it is proposed that the browser module is configured to track and prepare for display, in particular on a display device associated with the knowledge asset distribution platform, an origin report of a package of knowledge assets or of a content of the package of knowledge assets and/or of a schema associated with at least one knowledge asset and/or with at least one package of knowledge assets. Thus, a provenance of knowledge assets and/or packages of knowledge assets may advantageously be tracked, in particular facilitating a traceability of modifications, deletions, additions or replacements of knowledge assets. Thereby a high degree of openness and accountability can be advantageously achieved. Furthermore, a high degree of reliability and a high degree of content quality may advantageously be achieved, which in particular allows an excellent quality control with a very high level of precision. The origin report in particular comprises at least date, time and/or author of each modification, deletion, addition and/or replacement of a knowledge asset or of a metadata, in particular of each instance of a knowledge asset or of each schema associated with a knowledge asset. A separate origin report is in particular associated with each knowledge asset, in particular each instance of knowledge asset, each metadata and/or each schema. The origin reports are in particular stored within the non-transitory memory unit of the knowledge asset distribution platform and are accessible via the browser module. Preferably all origin reports, associated with any component of a distributed package of knowledge assets are attached to and/or included in the distributed package of knowledge assets and are transmitted in conjunction with the distributed package of knowledge assets when transferred to a CSE via the sender module.

Furthermore, it is proposed that the browser module comprises an assessment platform, which is configured to provide at least a validity assessment functionality, an applicability assessment functionality and/or a reputation assessment functionality for the packages of knowledge assets which are to be distributed, wherein the content of the assessment platform is accessible for users, in particular providers and/or consumers, of the knowledge asset distribution platform. Thus, a high degree of content quality is advantageously achievable, in particular leading to a high degree of reliability of the content which is to be distributed by the knowledge asset distribution platform. An "assessment platform" is in particular to be understood as a platform which comprises at least a rating platform, in particular a user rating platform and/or an expert rating platform, a commenting platform, a discussion platform and/or an issue reporting platform. A "validity assessment functionality" is in particular to mean a functionality intended to at least collect, evaluate and/or publish information about a validity of a content of packages of knowledge assets which are available via the knowledge asset distribution platform. An "applicability assessment functionality" is in particular to mean a functionality intended to at least collect, evaluate and/or publish information about an applicability of a content of packages of knowledge assets which are available via the knowledge asset distribution platform. A "reputation assessment functionality" is in particular to mean a functionality intended to at least collect, evaluate and/or publish information about a reputation of providers of packages of knowledge assets which are available via the knowledge asset distribution platform. Users of the knowledge asset distribution platform, in particular providers and/or consumers, are preferably entitled to read and/or write ratings, comments and/or discussion posts, which are visible to other users. In addition, the assessment platform is in particular configured to include additional evaluation metrics in an assessment, e.g. of an applicability or similar. For example, an additional evaluation metric is a usage frequency or a usage characteristic of knowledge assets of a package of knowledge assets. Other possible additional evaluation metrics comprise, amongst others, a level of complexity of a package of knowledge assets, of the content of a package of knowledge assets or of an underlying model (schema) of a package of knowledge assets, a complexity of integration of a package of knowledge assets in an existing KMSE, a maintenance frequency of a package of knowledge assets, an estimated maintenance cost of a package of knowledge assets or a compatibility of a package of knowledge assets with an already existing CSE.

In addition, it is proposed that the knowledge assets are bio-medical and/or clinical knowledge assets, wherein the knowledge asset distribution platform is configured to distribute bio-medical and/or clinical knowledge assets. Thus, advantageous characteristics regarding a targeted distribution of bio-medical and/or clinical knowledge assets, in particular regarding a sending, a receiving and/or a relaying of packages of knowledge assets between different computer systems, in particular between different bio-medical and/or clinical PSEs and/or bio-medical and/or clinical CSEs are advantageously achievable. The term "bio-medical" is in particular to mean related to sciences dealing with healthcare or with public health. The term "clinical" is in particular to mean related to an observation and/or a treatment of patients.

Moreover, a computer-implemented method for distributing packages of knowledge assets between a plurality of, in particular mutually compatible, provider system environments (PSE) and/or consumer system environments (CSE), which are adapted to store knowledge assets and to make the knowledge assets available to users of the CSEs via a knowledge asset distribution platform is proposed, the knowledge asset distribution platform comprising at least one processor unit, with at least one non-transitory memory unit, and with a distribution module, which is configured to distribute packages of knowledge assets at least in the following steps: selecting a scope and/or a content of a package of knowledge assets which are to be distributed, via the knowledge asset distribution platform, from a pool of knowledge assets available within at least one PSE, receiving packages of knowledge assets to be distributed by the knowledge asset distribution platform from at least one PSE, and/or receiving content information of the packages of knowledge assets to be distributed by the knowledge asset distribution platform from the at least one PSE, storing packages of knowledge assets and/or storing content information on packages of knowledge assets, in particular the packages of knowledge assets and/or the content information received in a previous step, within the non-transitory memory unit, providing a browser function for browsing the knowledge assets stored within the non-transitory memory and/or for browsing the content information stored within the non-transitory memory for the purpose of finding and/or locating specific packages of knowledge assets and/or for finding and/or locating packages of knowledge assets containing knowledge about specific topics, and relaying packages of knowledge assets, in particular selected by a user, from the non-transitory memory unit and/or from the at least one PSE to at least one CSE. In this way advantageous characteristics regarding a targeted distribution of knowledge assets, in particular regarding a sending, a receiving and/or a relaying of packages of knowledge assets between different computer systems, in particular between different PSEs and/or CSEs, are advantageously achievable. In particular, a high degree of customizability of packages of knowledge assets to be distributed may advantageously be provided, thus advantageously allowing a particularly effective usage of network resources, e.g. a bandwidth, a data volume to be transmitted and/or a particularly high usability of the knowledge asset distribution platform, due to the fact that the knowledge assets of the packages of knowledge assets to be distributed may advantageously be grouped according to freely definable characteristics.

A computer-implemented knowledge asset distribution platform according to the invention and a computer-implemented method for distributing packages of knowledge assets according to the invention are herein not to be restricted to the applications and implementation forms described above. In particular, to fulfill a functionality herein described, the computer-implemented knowledge asset distribution platform according to the invention and the computer-implemented method for distributing packages of knowledge assets according to the invention may comprise a number of respective elements and/or structural components and/or units and/or method steps that differs from a number herein mentioned.

DRAWINGS

Further advantages will become apparent from the following description of the drawings. In the drawings an exemplary embodiment of the invention is depicted. The drawings, the description and the claims contain a plurality of features in combination. Someone skilled in the art will purposefully also consider the features separately and will find further expedient combinations.

Figure 2:
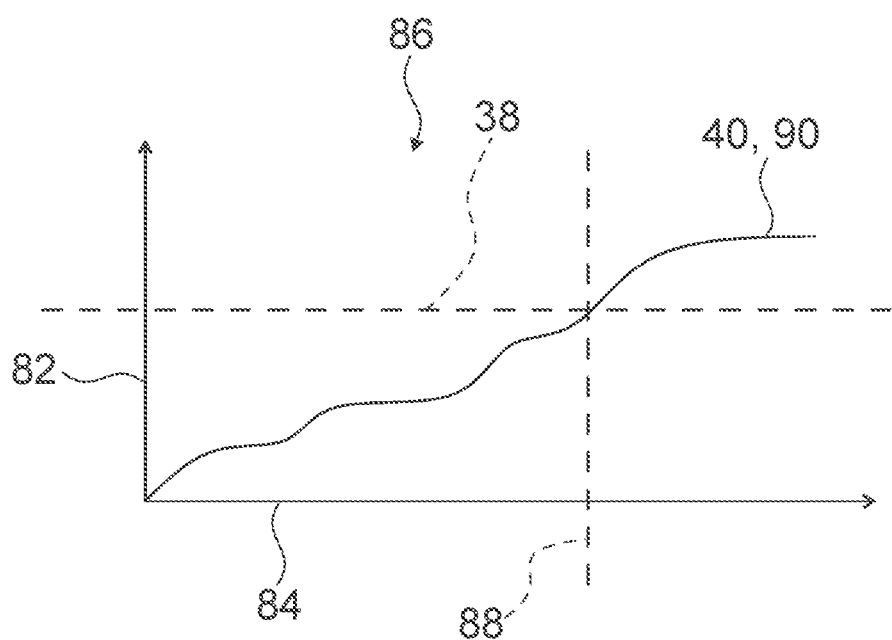
Figure 3:
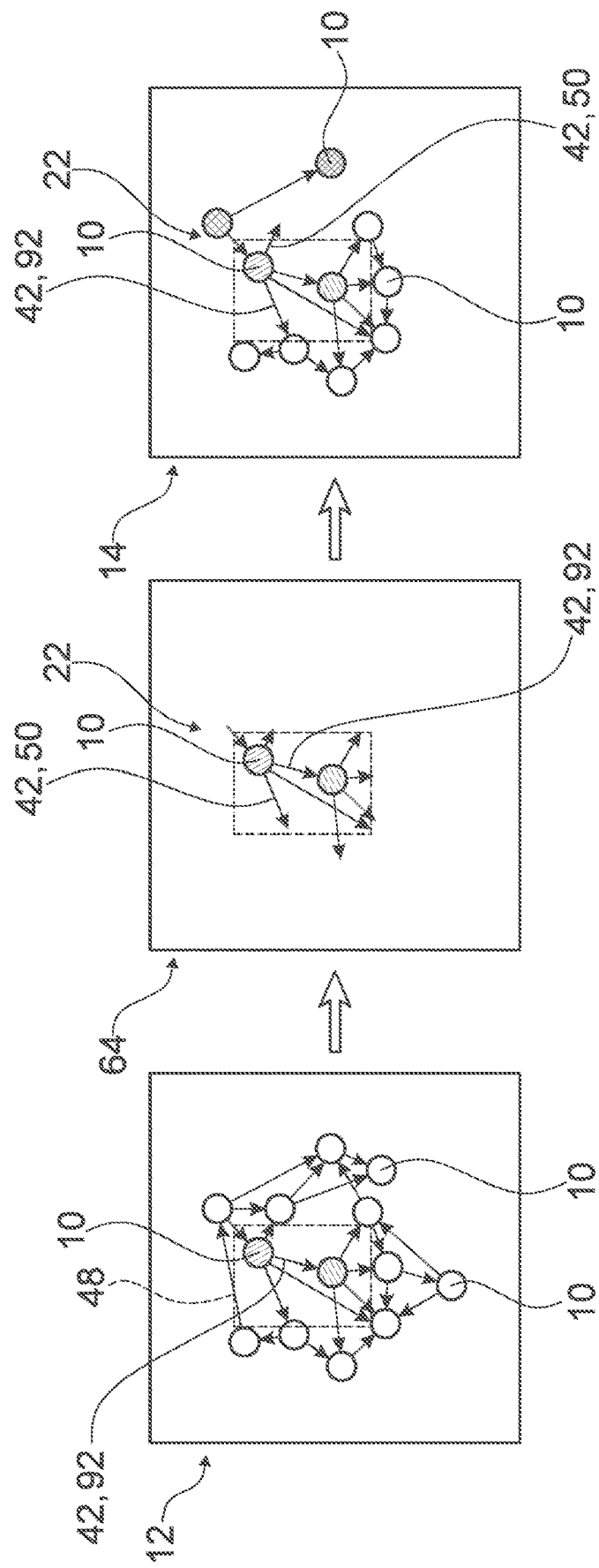
Figure 4:
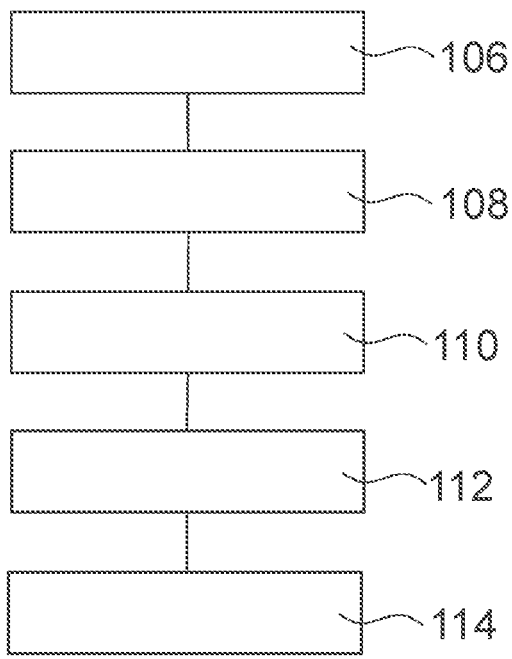
Figure 5:
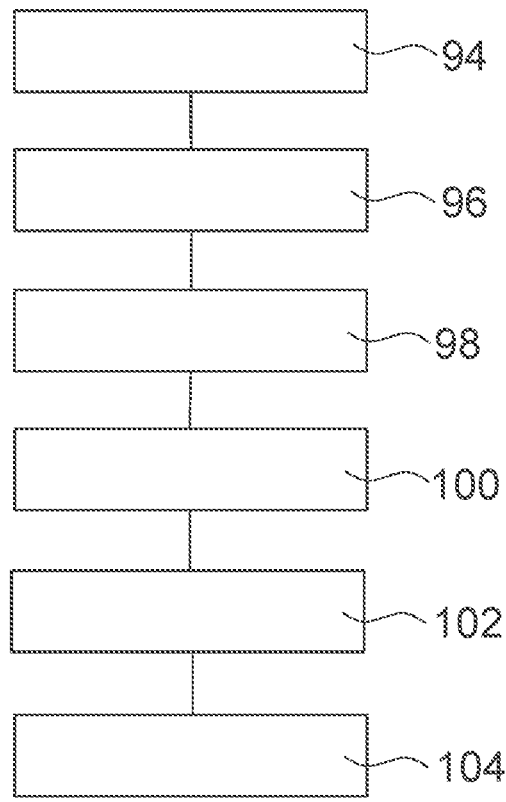
Figure 6:
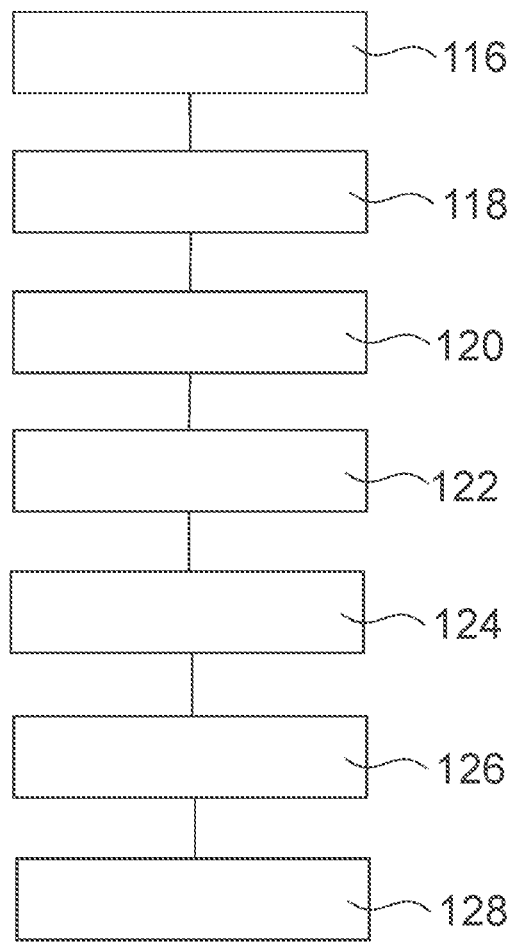
Figure 7:
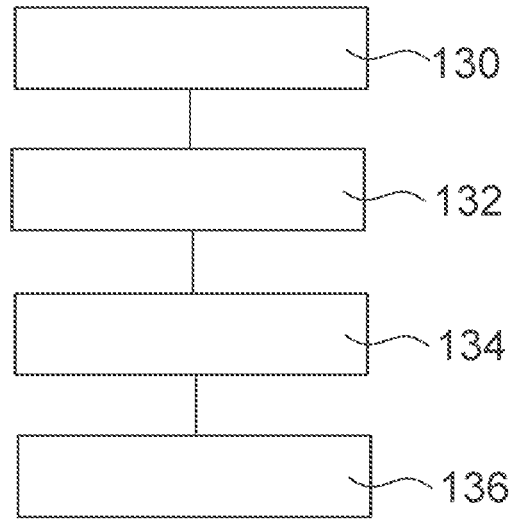
Figure 8:
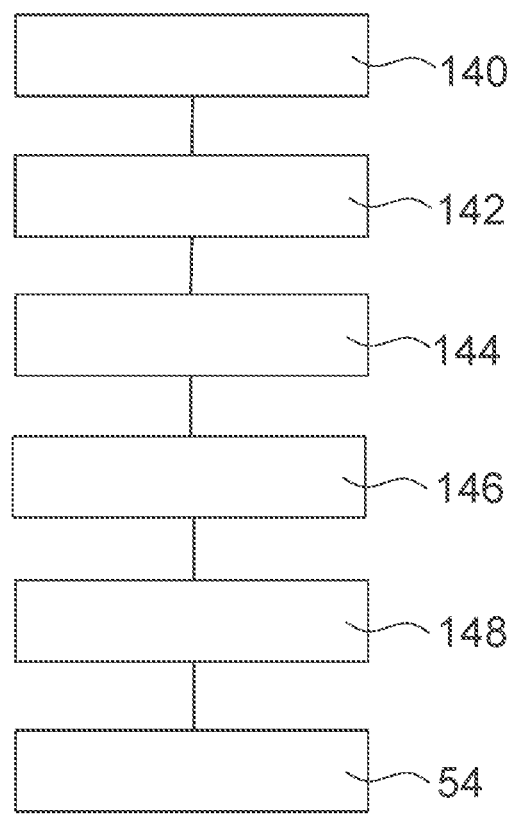
Figure 9:
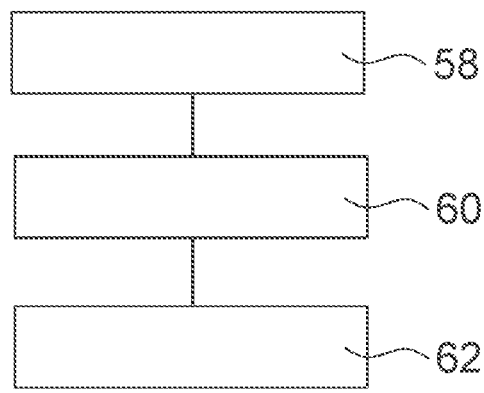

It is shown in:

FIG. 1 a schematic representation of a knowledge asset distribution platform,

FIG. 2 an exemplary diagram of a relevance indicator,

FIG. 3 a schematic representation of an export of a package of knowledge assets from a provider system environment (PSE) to the knowledge asset distribution platform (left side) and a schematic representation of an import of a package of knowledge assets from the knowledge asset distribution platform to a consumer system environment (CSE, right side), FIG. 4 a flowchart of a computer-implemented method for distributing the packages of knowledge assets between a plurality of PSEs and CSEs, FIG. 5 a flowchart of an update procedure of the packages of knowledge assets previously distributed by the knowledge asset distribution platform, FIG. 6 a flowchart of a procedure for exporting and/or acquiring a package of knowledge assets from the PSE, FIG. 7 a flowchart of a procedure for importing and/or integrating a package of knowledge assets containing weak links to the CSE, FIG. 8 a flowchart of a linkage procedure, and FIG. 9 a flowchart of an integrity checking procedure.

DESCRIPTION OF THE EXEMPLARY EMBODIMENTS

FIG. 1 shows a schematic representation of a computer-implemented knowledge asset distribution platform 64. The knowledge asset distribution platform 64 comprises a processor unit 16. The processor unit 16 is configured to provide computational power in order to operate the knowledge asset distribution platform 64. The knowledge asset distribution platform 64 comprises a non-transitory memory unit 18. The non-transitory memory unit 18 is configured to contain instructions for operating and organizing the knowledge asset distribution platform 64 when executed by the processor unit 16. The non-transitory memory unit 18 is configured to store data related to the knowledge asset distribution platform 64. The non-transitory memory unit 18 is configured to at least store packages of knowledge assets 22. The knowledge asset distribution platform 64 is configured to distribute packages of knowledge assets 22. The knowledge asset distribution platform 64 is configured to distribute packages of knowledge assets 22 between a plurality of provider entities 66 and a plurality of consumer entities 68. The provider entities 66 provide packages of knowledge assets 22 which are to be distributed by the knowledge asset distribution platform 64. The consumer entities 68 consume packages of knowledge assets 22 which are offered by the knowledge asset distribution platform 64.

The packages of knowledge assets 22 comprise at least one knowledge asset 10. The knowledge asset 10 is implemented as a collection of information about a specific topic. In this embodiment, the knowledge asset 10 is implemented as a bio-medical knowledge asset and/or a clinical knowledge asset. Each package of knowledge assets 22 comprises at least one instance of a knowledge asset 32. Each knowledge asset 10 comprises at least one instance of a knowledge asset 32. The instance of the knowledge asset 32 is a version of the content of the knowledge asset 10 at a specific point in time. While a knowledge asset 10 may comprise several instances of knowledge assets 32, only one instance of the knowledge asset 32 represents a currently valid instance of the knowledge asset 32. Whenever the currently valid instance of the knowledge asset 32 is modified, a new instance of the knowledge asset 32 is created and may, upon verification by at least one competent user, replace the currently valid instance of the knowledge asset 32. The package of knowledge assets 22 comprises at least one schema of a knowledge asset 34. The package of knowledge assets 22 is attributed at least a schema of a knowledge asset 34. The schema of the knowledge asset 34 defines a model and/or structure of a knowledge management system environment (KMS) applicable to this package of knowledge assets 22.

The knowledge asset distribution platform 64 is configured to distribute packages of knowledge assets 22 between a plurality of provider system environments (PSE) 12 and a plurality of consumer system environments (CSE) 14. The PSE 12 represents a knowledge management system environment (KMSE) operated by computer systems of the provider entity 66. The provider entity 66 may be at least one of the group of hospitals, bio-medical research institutes, bio-medical organizations, government agencies, private corporations or similar. The PSE 12 is configured to at least store knowledge assets 10 and to make the knowledge assets 10 available to users of the PSE 12. The PSE 12 contains a pool of knowledge assets 10. The CSE 14 represents a knowledge management system environment (KMSE) operated by computer systems of the consumer entity 68. The consumer entity 68 may be at least one of the group of hospitals, bio-medical research institutes, bio-medical organizations, government agencies, private corporations, medical practices or similar. The CSE 14 is configured to at least store knowledge assets 10 and to make the knowledge assets 10 available to users of the CSE 14. The computer systems of the knowledge asset distribution platform 64 also operate a KMSE. The PSE 12, the KMSE of the knowledge asset distribution platform 64 and the CSE 14 may be different, at least partially incompatible computer system environments. Alternatively, the PSE 12, the KMSE of the knowledge asset distribution platform 64 and the CSE 14 may be mutually compatible computer system environments.

The knowledge asset distribution platform 64 comprises a distribution module 20. The distribution module 20 is configured to distribute packages of knowledge assets 22. The distribution module 20 comprises a receiver module 24. The receiver module 24 is configured to receive packages of knowledge assets 22 from the PSE 12. The packages of knowledge assets 22 received by the receiver module 24 are configured to be distributed by the knowledge asset distribution platform 64. The receiver module 24 comprises a receiver device 72. The receiver device 72 is configured to receive data packages, in particular knowledge assets 10, implemented as physical signals, e.g. electric, electromagnetic or optical signals. The receiver device 72 is configured to interpret the data packages and to relay them to a database module 26 for storage within the non-transitory memory unit 18. The receiver module 24 is configured to receive content information on the packages of knowledge assets 22 to be distributed by the knowledge asset distribution platform 64 from the at least one PSE 12. The content information serves for information purposes for consumer entities 68 interested in acquiring a specific package of knowledge assets 22. The distribution module 20 is implemented integrally with a computer system of the knowledge asset distribution platform 64. The distribution module 20 is operated by the processor unit 16, based on instructions stored in the non-transitory memory unit 18. A scope and/or a content of the packages of knowledge assets 22 to be distributed via the knowledge asset distribution platform 64 is definable by a user of the PSE 12 from the pool of knowledge assets 10 available within the PSE 12. The receiver module 24 comprises an acquisition module 46. The acquisition module 46 is configured to acquire from a PSE 12 at least a portion of knowledge assets 48 of a pool of knowledge assets 10 available in the PSE 12. The acquisition module 46 is configured to arrange a transfer of the acquired packages of knowledge assets 22 from the PSE 12 to the knowledge asset distribution platform 64.

The knowledge asset distribution platform 64 comprises a database module 26. The database module 26 is configured to store packages of knowledge assets 22 within the non-transitory memory unit 18. The database module 26 is configured to store content information of packages of knowledge assets 22, in particular the packages of knowledge assets 22 and/or the content information received by the receiver module 24, within the non-transitory memory unit 18. The database module 26 is implemented integrally with the computer system of the knowledge asset distribution platform 64. The database module 26 is operated by the processor unit 16, based on instructions stored in the non-transitory memory unit 18. The database module 26 controls access to data stored within the non-transitory memory unit 18. The database module 26 is configured to file data, in particular knowledge assets 10, received by the receiver module 24 in the non-transitory memory unit 18. The database module 26 is configured to read data, in particular knowledge assets 10, which are to be sent out by a sender module 30 from the non-transitory memory unit 18. In particular, it is conceivable that the sender module 30, the database module 26, the receiver module 24 and/or a browser module 28 are all at least partly components of a single multifunctional computer and/or software module.

The knowledge asset distribution platform 64 comprises a browser module 28. The browser module 28 is configured to provide a browser function for browsing the knowledge assets 10 and/or the packages of knowledge assets 22 stored by the database module 26. The browser module 28 is configured to provide a browser function for browsing the knowledge assets 10 and/or the packages of knowledge assets 22 stored within the non-transitory memory unit 18. The browser module 28 is configured to provide a browser function for browsing the content information stored by the database module 26 or within the non-transitory memory unit 18. The browser function is configured to find and/or locate specific knowledge assets 10 and/or specific packages of knowledge assets 22 and/or to find and/or locate packages of knowledge assets 22 containing knowledge about specific topics. The browser module 28 is implemented integrally with the computer system of the knowledge asset distribution platform 64. The browser module 28 is operated by the processor unit 16, based on instructions stored in the non-transitory memory unit 18. The browser module 28 interacts with the database module 26. The knowledge asset distribution platform 64 comprises a display device 56. Alternatively, the display device could be implemented external to the knowledge asset distribution platform 64, e.g. partly on the side of the consumer entity 68 or on the side of the provider entity 66. The browser module 28 is configured to prepare and transmit data, e.g. content information about packages of knowledge assets 22 or search results from a search performed by the browser module 28, to the display device 56 for graphical and/or textual representation. The browser module 28 is configured to create and prepare for display at least one ranked list of related packages of knowledge assets 22 which are available to be distributed via the knowledge asset distribution platform 64, wherein a rank of the ranked list depends on a total number of weak links 50 (see also FIG. 3), which are potentially re-connectable by a combination of the package of knowledge assets 22 with the respective related package of knowledge assets 22.

The knowledge asset distribution platform 64 comprises a sender module 30. The sender module 30 is configured to relay packages of knowledge assets 22, which have in particular been selected by a user via the browser module 28, from the non-transitory memory unit 18 and/or directly from the PSE 12 to the CSE 14. The sender module 30 comprises a sender device 70. The sender device 70 is configured to prepare and transmit and/or send out electronic data. The sender device 70 is configured to send out the data via a physical data connection, e.g. a cable. Alternatively, the sender device 70 may be configured to send out data via a wireless data connection, e.g. a WLAN connection. The sender module 30 comprises a consumer import module 52. The consumer import module 52 is configured to import into the CSE 14 packages of knowledge assets 22 transferred to a CSE 14 by the sender device 70. The consumer import module 52 is configured to integrate the imported packages of knowledge assets 22 in an existing set of knowledge assets 10 already available in the CSE 14. The consumer import module 52 comprises a linkage unit 138. The linkage unit 138 is configured to guide a user at least semi-automatically through a linkage process for a re-connection and/or a removal of weak links 50 during an import of a package of knowledge assets 22 in the CSE 14. The linkage unit 138 is configured to search the existing knowledge assets 10 of the CSE 14. The linkage unit 138 is configured to compare at least one characteristic of the existing knowledge assets 10 of the CSE 14 to at least one characteristic of a weak link 50. The linkage unit 138 is configured to create a list of probable target knowledge assets for the weak link 50 on the basis of the existing knowledge assets 10 of the CSE 14. The linkage unit 138 is configured to display the list of probable target knowledge assets to a user of the CSE 14 for selection.

The knowledge asset distribution platform 64 comprises an interface module 44. The interface module 44 is configured to allow remote access to packages of knowledge assets 22 distributed by the distribution module 20. The interface module 44 allows the remote access via the Internet 78. The interface module 44 allows the remote access via a web browser. The interface module 44 is implemented as a display device 56. The display device 56 comprises a display 74. The display device 56 is configured to display data prepared by the browser module 28. The display device 56 is configured to send commands and/or instructions to the distribution module 20, in particular to the browser module 28. The display device 56 is implemented as an, in particular portable, computing device, e.g. a smartphone, a tablet, a laptop or similar. The browser module 28 is configured to create and prepare for display, for example with the display device 56, at least one ranked list of related packages of knowledge assets 22 which are to be distributed via the knowledge asset distribution platform 64. The browser module 28 is configured to track and prepare for display, for example via the display device 56, an origin report of a package of knowledge assets 22 or of a content of the package of knowledge assets 22 and/or of a schema 34 associated with at least one knowledge asset 10.

The browser module 28 comprises an assessment platform 76. The assessment platform 76 is configured to provide at least a validity assessment functionality for the packages of knowledge assets 22 which are to be distributed by the knowledge asset distribution platform 64. The assessment platform 76 is configured to provide at least an applicability assessment functionality for the packages of knowledge assets 22 which are to be distributed by the knowledge asset distribution platform 64. The assessment platform 76 is configured to provide at least a reputation assessment functionality for the packages of knowledge assets 22 which are to be distributed by the knowledge asset distribution platform 64. A content of the assessment platform 76 is accessible for users of the knowledge asset distribution platform 64, e.g. via the display device 56 or via the Internet 78.

The distribution module 20 comprises a tracker module 36. The tracker module 36 is configured to monitor an up-to-dateness of a package of knowledge assets 22 relayed to at least one CSE 14 via the sender module 30. The tracker module 36 comprises at least one watcher module 80. The watcher module 80 is configured to be implemented in an external CSE 14. The watcher module 80 is configured to capture a state of the knowledge assets 10 and/or a state of the packages of knowledge assets 22 of the CSE 14, in particular the state of the knowledge assets 10 and/or a state of the packages of knowledge assets 22 of the CSE 14 previously transferred to the CSE 14 via the knowledge asset distribution platform 64. The watcher module 80 is configured to relay information about the state and/or the up-to-dateness of the monitored knowledge assets 10 or the packages of knowledge assets 22 to the knowledge asset distribution platform 64, in particular to the browser module 28. The tracker module 36 is configured to send out an update signal to the CSE 14 when a relevance indicator 40 (see also FIG. 2) of a package of knowledge assets 22 reaches or surpasses a predetermined condition 38. The tracker module 36 is configured to relay an updated version of a previously relayed and now out-of-date package of knowledge assets 22 to the CSE 14 via the sender module 30. The tracker module 36 is configured to detect modifications of knowledge assets 10 within the package of knowledge assets 22 to be updated, executed on the side of the CSE 14. The tracker module 36 is configured to detect modifications of links 42 between knowledge assets 10 within the package of knowledge assets 22 to be updated, executed on the side of the CSE 14.

FIG. 2 shows a diagram 86 of the relevance indicator 40 for a specific package of knowledge assets 22 monitored by the tracker module 36. The diagram 86 comprises an abscissa 84 and an ordinate 82. The abscissa 84 shows a time elapsed since the most recent update of the specific package of knowledge assets 22. The ordinate 82 shows the relevance indicator 40. The relevance indicator 40 of a package of knowledge assets 22 is a percentage of knowledge assets 10 which have changed since a preceding transmission of the package of knowledge assets 22 to a monitored CSE 14. The relevance indicator 40 is implemented as a value of a relevance parameter 90. The relevance parameter 90 is determined by the tracker module 36 for a package of knowledge assets 22 upon each update of at least one knowledge asset 10 of the package of knowledge assets 22 in the database of the knowledge asset distribution platform 64 via a comparison of the most recent version of the specific package of knowledge assets 22 available in the knowledge asset distribution platform 64 and the version of the specific package of knowledge assets 22 available in the monitored CSE 14. The value of the relevance parameter 90 varies, in particular increases with time and/or with increasing difference between the most recent version of the specific package of knowledge assets 22 available in the knowledge asset distribution platform 64 and the version of the specific package of knowledge assets 22 available in the monitored CSE 14. The tracker module 36 is configured to send out an update signal to the CSE 14 when the relevance indicator 40 of a package of knowledge assets 22 reaches or surpasses a predetermined condition 38. The predetermined condition 38 is implemented as a maximum value of the relevance parameter 90. The predetermined condition 38 is a threshold. The predetermined condition 38 is a maximum percentage of knowledge assets 10 which have changed since a preceding transmission of the package of knowledge assets 22 to the monitored CSE 14. On the ordinate 82 of the diagram 86 the predetermined condition 38 is indicated by a dashed line. At a specific point in time 88 the predetermined condition 38 is reached. The point in time 88 is indicated by an intersection of another dashed perpendicular line with the abscissa 84 of the diagram 86. At the point in time 88 the update signal is sent to the CSE 14, in particular to a user of the CSE 14, e.g. via the display device 56.

FIG. 3 shows a schematic representation of an export of a package of knowledge assets 22 from a PSE 12 to the knowledge asset distribution platform 64 (left side) and a schematic representation of an import of a package of knowledge assets 22 from the knowledge asset distribution platform 64 to a CSE 14 (right side). The PSE 12 shown on the left side of FIG. 3 comprises a number of knowledge assets 10 which are interlinked by links 42. Each link 42 comprises a pointer. All links 42 of the PSE 12 connect at least two knowledge assets 10. Links 42 connecting at least two knowledge assets 10 are identified as strong links 92. Upon an acquisition of a package of knowledge assets 22 from the PSE 12 via the acquisition module 46, a selection is made of a portion of the knowledge assets 48 of the PSE 12 which are to be grouped in a package of knowledge assets 22. The acquisition module 46 creates a copy of the selected knowledge assets 10 and of all connected links and attributes of the selected knowledge assets 10. The acquisition module 46 unlinks all links 42 connecting a selected knowledge asset 10 to a knowledge asset 10 which was not selected. Unlinked links 42 of a knowledge asset 10 are identified as weak links 50. The newly created package of knowledge assets 22, which is to be distributed by the knowledge asset distribution platform 64 shown in the middle of FIG. 3, contains several weak links 50. The newly created package of knowledge assets 22, which is to be distributed by the knowledge asset distribution platform 64 shown in the middle of FIG. 3, contains at least one strong link 92. The CSE 14 shown on the right side of FIG. 3 comprises the package of knowledge assets 22 acquired from the PSE 12 and a number of knowledge assets 10 which were already present before the new package of knowledge assets 22 was included, in particular imported. A fraction of the weak links 50 of the newly included package of knowledge assets 22 are re-connected with knowledge assets 10 of the CSE 14 that were already available before the import in an at least semi-automatic linkage process. Re-connected weak links 50 are converted into strong links 92. A further fraction of the weak links 50 of the newly included package of knowledge assets 22 are not re-connected. The non-re-connected weak links 50 have no suitable partnering knowledge asset 10 in the CSE 14. The non-re-connected weak links 50 are attributed and/or flagged with exceptional values in the linkage process.

FIG. 4 shows a flowchart of a computer-implemented method for distributing packages of knowledge assets 22 between a plurality of PSEs 12 and/or CSEs 14. A distribution of packages of knowledge assets 22 comprises a number of distribution steps 106, 108, 110, 112, 114. In at least one distribution step 106 a scope and/or a content of at least one package of knowledge assets 22 which is to be distributed via the knowledge asset distribution platform 64 is selected from a pool of knowledge assets 10 available within a PSE 12. The scope and/or the content of the at least one package of knowledge assets 22 to be distributed via the knowledge asset distribution platform 64 is defined in the distribution step 106 by a user of the PSE 12 from the pool of knowledge assets 10 available within the PSE 12. In at least one further distribution step 108 the packages of knowledge assets 22 to be distributed by the knowledge asset distribution platform 64 and/or content information of the packages of knowledge assets 22 to be distributed by the knowledge asset distribution platform 64 are/is received from the PSE 12. In at least one further distribution step 110, the packages of knowledge assets 22 and/or the content information on the packages of knowledge assets 22, which were in particular received in the previous distribution step 108, are stored within the non-transitory memory unit 18. In at least one further distribution step 112, a browser function for browsing the knowledge assets 10 and/or the packages of knowledge assets 22 stored within the non-transitory memory 18, in particular in one of the previous distribution steps 110, and/or for browsing the content information stored within the non-transitory memory 18 is provided for the purpose of finding and/or locating specific knowledge assets 10 and/or specific packages of knowledge assets 22 and/or for finding and/or locating packages of knowledge assets 22 containing knowledge about specific topics. In a further distribution step 114, the package of knowledge assets 22, which is in particular selected by a user of the CSE 14, in particular in the previous distribution step 112, is relayed from the non-transitory memory unit 18 to the CSE 14.

FIG. 5 shows a flowchart of an update procedure of packages of knowledge assets 22 which were previously distributed by the knowledge asset distribution platform 64. In at least one update step 94, the relevance indicator 40 of a package of knowledge assets 22 is determined by the tracker module 36 by a comparison of versions of knowledge assets 10 within the CSE 14 and within the knowledge asset distribution platform 64. In the update step 94, the relevance indicator 40 is determined by the tracker module 36 for the package of knowledge assets 22 upon each update of at least one knowledge asset 10 of the package of knowledge assets 22 within the database of the knowledge asset distribution platform 64. In at least one further update step 96, the relevance parameter 90 is calculated. When calculating the relevance parameter 90 in the further update step 96, the tracker module 36 performs a weighting and/or a judging of a type or an extent of a detected change of the knowledge asset 10 of the updated package of knowledge assets 22. In at least one further update step 98, an update signal is sent out by the tracker module 36 to the CSE 14, in particular to a user of the CSE 14, if the relevance indicator 40, in particular the calculated relevance parameter 90, of the package of knowledge assets 22 reaches or surpasses the predetermined condition 38. The predetermined condition 38 comprises a set of alert conditions corresponding to particular relevance parameter definitions. In at least one further update step 100, the tracker module 36 relays an updated version of the previously relayed and now out-of-date package of knowledge assets 22 to the CSE 14. In at least one further update step 102, the tracker module 36 searches for modifications of knowledge assets 10 within the package of knowledge assets 22 to be updated, which were introduced on the side of the CSE 14. In the further update step 102, the tracker module 36 searches for modifications of links 42 between knowledge assets 10 within the package of knowledge assets 22 to be updated, which were introduced on the side of the CSE 14. In at least one further update step 104, the tracker module 36 seeks a user confirmation from a user of the CSE 14, in order to determine whether a modified knowledge asset 10 or a modified link 42 may be overwritten and/or replaced. In the further update step 104 the tracker module 36 prompts a query, requesting confirmation or rejection of an overwriting or a replacing, before the knowledge asset 10 or the link 42 with the detected modification is overwritten and/or replaced.

FIG. 6 shows a flowchart of a procedure for exporting and/or acquiring a package of knowledge assets 22 from a PSE 12. In at least one acquisition step 116 knowledge assets 10 belonging to a portion of knowledge assets 48 which are to be acquired from the PSE 12, including all links 42 and attributes connected with the knowledge assets 10 of said portion of knowledge assets 48 are identified manually or at least semi-automatically. In this acquisition step 116 the package of knowledge assets 22 to be acquired is defined. In at least one further acquisition step 118, a (virtual) copy of the portion of knowledge assets 48, which were in particular identified in the previous acquisition step 116, is created. In at least one further acquisition step 120, all links 42 connecting knowledge assets 10 of said identified portion of knowledge assets 48 with knowledge assets 10 of the PSE 12 lying outside the identified portion of knowledge assets 48 are identified. In at least one further acquisition step 122, the identified links 42 of the (virtual) copy of the portion of knowledge assets 48, which was in particular created in the previous acquisition step 120, are tagged as weak links 50. In at least one further acquisition step 124, the (virtual) copy of knowledge assets is converted in a package of knowledge assets 22, which is in particular ready for a distribution by the knowledge asset distribution platform 64. In at least one further acquisition step 126, the package of knowledge assets 22 is transmitted to the knowledge asset distribution platform 64 and/or stored within the non-transitory memory unit 18 of the knowledge asset distribution platform 64. In at least one further acquisition step 128, the copy of knowledge assets 10 from the PSE 12, including all strong (intact) links 92 between knowledge assets 10 and including the weak links 50, is rendered available for access via the knowledge asset distribution platform 64, in particular for a subsequent relaying to the CSE 14 via the sender module 30.

FIG. 7 shows a flowchart of a procedure for importing and/or integrating a package of knowledge assets 22 containing weak links 50 to a CSE 14. In at least one integration step 130, a package of knowledge assets 22 to be imported is copied from the non-transitory memory unit 18 of the knowledge asset distribution platform 64 to a database of a CSE 14. In at least one further integration step 132, all weak links 50 connecting knowledge assets 10 of the package of knowledge assets 22 to be imported with target knowledge assets outside said package of knowledge assets 22 are identified. Alternatively or additionally, in this further integration step 132, all links 42 tagged as weak links 50, in particular all links 42 with a weak link tag, and/or the properties and/or attributes of the target knowledge assets of the weak links 50 are identified. In at least one further integration step 134, knowledge assets 10 already available in the CSE 14 are searched in order to find already available knowledge assets 10 which correspond to target knowledge assets and/or to knowledge assets 10 which are suitable to re-connect a weak link 50, in particular which share at least a large fraction of the properties and/or the attributes of the target knowledge assets. In at least one further integration step 136, at least a portion of the weak links 50 is re-connected by re-connecting at least a portion of the weak links 50. In the integration step 136, strong links 92 connecting the respective knowledge assets 10 of the package of knowledge assets 22 to said corresponding target knowledge assets are re-established, in particular following a linkage procedure.

In FIG. 8 a flowchart of the linkage procedure is shown. The linkage procedure comprises a number of linkage steps 140, 142, 144, 146, 148, 54. In the linkage procedure weak links 50 of a package of knowledge assets 22 containing weak links 50, which is imported into a CSE 14, are re-connected. In at least one linkage step 140 existing knowledge assets 10 of the CSE 14 are searched and/or catalogized. In at least one further linkage step 142, at least one characteristic of the existing knowledge assets 10 of the CSE 14 are compared to at least one characteristic of a weak link 50. The characteristic may be a content of the existing knowledge asset 10, an identifier, e.g. an LSID, of the existing knowledge asset 10 or similar. In at least one further linkage step 144 a list, in particular a ranked list, of probable target knowledge assets which are potentially suitable for re-connecting the weak link 50 is created on the basis of the existing knowledge assets 10 of the CSE 14. In at least one further linkage step 146, the list of probable target knowledge assets is displayed to a user of the CSE 14 for a selection of the target knowledge asset used to re-connect the weak link 50. In at least one further linkage step 148, an exceptional value is inserted in the knowledge asset 10, in particular in the link 42, preferably the weak link 50 associated with the knowledge asset 10, indicating that it has not been possible to establish the connection of the weak link 50. The exceptional value is inserted into the knowledge asset 10, in particular in the link 42, preferably the weak link 50 associated with the knowledge asset 10, if a weak link 50 of a knowledge asset 10 is not re-connected in the linkage procedure. In at least one further linkage step 54, a ranked list is created and presented to a user of the CSE 14, displaying at least related packages of knowledge assets 22 which are to be distributed via the knowledge asset distribution platform 64, wherein a rank of the ranked list depends on a total number of weak links 50 which are potentially re-connectable by a combination of the package of knowledge assets 22 with the respective related package of knowledge assets 22.

FIG. 9 shows a flowchart of an integrity checking procedure. The integrity checking procedure comprises a number of checking steps 58, 60, 62. In the integrity checking procedure, it is ensured that an import of a package of knowledge assets 22 in an existing CSE 14 does not lead to inconsistencies or logical errors. In at least one checking step 58, before inserting the exceptional value in the knowledge asset 10, an integrity of an imported knowledge asset 10 and/or an imported package of knowledge assets 22 is reviewed by reassessing compliance with at least one integrity constraint, e.g. at least one semantic integrity constraint and/or at least one structural integrity constraint. In this checking step 58, the insertion of the exceptional value is prevented if the integrity constraint would be violated by the insertion of the exceptional value. In at least one further checking step 60, the consumer import module 52 transitions from an automatic import mode into an at least semi-automatic import mode upon detection of a violation of an integrity constraint. In this case, in the checking step 60 a notification requesting user guidance is sent out to the user of the CSE 14. Furthermore, in this case in the checking step 60 a notification to the browser module 28 of the knowledge asset distribution platform 64 is sent out. In at least one further checking step 62, upon receiving the notification the browser module 28, in particular automatically, initiates a search for at least one knowledge asset 10 and/or at least one knowledge package, which is suitable for at least partially resolving the violation of the integrity constraint. In this further checking step 62, a notification is transmitted to the user of the CSE 14 suggesting required knowledge assets 10, required packages of knowledge assets 22 and/or required knowledge packages.

REFERENCE NUMERALS

10 Knowledge asset
12 Provider system environment
14 Consumer system environment
16 Processor unit
18 Non-transitory memory unit
20 Distribution module
22 Package of knowledge assets
24 Receiver module
26 Database module
28 Browser module
30 Sender module
32 Instance of a knowledge asset
34 Schema of a knowledge asset
36 Tracker module
38 Predetermined condition
40 Relevance indicator
42 Link
44 Interface module
46 Acquisition module
48 Portion of knowledge assets
50 Weak link
52 Consumer import module
54 Linkage step
56 Display device
58 Checking step
60 Checking step
62 Checking step
64 Knowledge asset distribution platform
66 Provider entity
68 Consumer entity
70 Sender device
72 Receiver device
74 Display
76 Assessment platform
78 Internet
80 Watcher module
82 Ordinate
84 Abscissa
86 Diagram
88 Point in time
90 Relevance parameter
92 Strong link
94 Update step
96 Update step
98 Update step
100 Update Step
102 Update Step
104 Update Step
106 Distribution step
108 Distribution step
110 Distribution step
112 Distribution step
114 Distribution step
116 Acquisition step
118 Acquisition step
120 Acquisition step
122 Acquisition step
124 Acquisition step
126 Acquisition step
128 Acquisition step
130 Integration step
132 Integration step
134 Integration step
136 Integration step
138 Linkage unit
140 Linkage step
142 Linkage step
144 Linkage step
146 Linkage step
148 Linkage Step

The invention claimed is:

1. A computer-implemented knowledge asset distribution platform, configured to distribute packages of knowledge assets between a plurality of provider system environments (PSE) and/or consumer system environments (CSE), which are configured to at least store knowledge assets and to make the knowledge assets available to users of the CSE, with at least one processor unit, with at least one non-transitory memory unit, and with a distribution module configured to distribute packages of knowledge assets and comprising:

a receiver module configured to receive packages of knowledge assets, which packages are configured to be distributed by the knowledge asset distribution platform from at least one PSE and/or to receive content information on the packages of knowledge assets to be distributed by the knowledge asset distribution platform from the at least one PSE, a database module configured to store packages of knowledge assets and/or to store content information of or about packages of knowledge assets, in particular the packages of knowledge assets and/or the content information received by the receiver module, within the non-transitory memory unit, a browser module which is configured to provide a browser function for browsing the knowledge assets stored by the database module and/or for browsing and/or finding the content information and/or metadata stored by the database module in order to find and/or locate specific packages of knowledge assets and/or to find and/or locate packages of knowledge assets containing knowledge about specific topics, and a sender module configured to relay packages of knowledge assets, from the non-transitory memory unit and/or from the at least one PSE to at least one CSE, wherein the scope and/or the content of a package of knowledge assets to be distributed via the knowledge asset distribution platform are/is definable by a user of the at least one PSE from a pool of knowledge assets available within the at least one PSE, wherein the receiver module comprises an acquisition module, which is configured to acquire at least a portion of a set of knowledge assets from the PSE, thereby defining a package of knowledge assets, and wherein the non-transitory memory unit comprises instructions that, when performed by the processor unit, make the acquisition module:

identify knowledge assets belonging to the portion of knowledge assets which are to be acquired from the PSE by the acquisition module, including at least all links and attributes connected with the knowledge assets of said portion of knowledge assets, identify all links connecting knowledge assets of said identified portion with knowledge assets of the PSE outside the identified portion of knowledge assets, create an, in particular virtual, copy of said identified portion of knowledge assets from the PSE, tag the identified links of said, in particular virtual, copy of knowledge assets as weak (at least semi-broken) links, and render the copy of knowledge assets from the PSE, including all strong (intact) links between knowledge assets and including the weak (at least semi-broken) links, available for access via the knowledge asset distribution platform, in particular for a subsequent relaying to a CSE via the sender module.

2. The computer-implemented knowledge asset distribution platform according to claim 1, wherein the package of knowledge assets comprises at least one instance of a knowledge asset and at least one schema of at least one knowledge asset.

3. The computer-implemented knowledge asset distribution platform according to claim 1, wherein the distribution module comprises a tracker module, which is configured to monitor the up-to-dateness of a package of knowledge assets which has been relayed via the sender module to at least one CSE.

4. The computer-implemented knowledge asset distribution platform according to claim 3, wherein the tracker module is configured to send out an update signal to the CSE when a relevance indicator of a package of knowledge assets reaches or surpasses a predetermined condition.

5. The computer-implemented knowledge asset distribution platform according to claim 4, wherein the relevance indicator of the package of knowledge assets is implemented as a relevance parameter, which is determined by the tracker module for a package of knowledge assets upon an update of at least one knowledge asset of the package of knowledge assets and which is established by the tracker module at least in part based at least on a weighting and/or a judging of a type or an extent of a detected change at least of the at least one updated knowledge asset of the package of knowledge assets, and wherein the predetermined condition is a set of alert conditions corresponding to particular relevance parameter definitions.

6. The computer-implemented knowledge asset distribution platform according to claim 4, wherein the relevance indicator of the package of knowledge assets is a percentage of knowledge assets which have changed since a preceding transmission of the package of knowledge assets to a respective CSE, and wherein the predetermined condition is a threshold, in particular a maximum percentage of knowledge assets which have changed since a preceding transmission of the package of knowledge assets to a respective CSE.

7. The computer-implemented knowledge asset distribution platform according to claim 3, wherein the tracker module is configured to relay an updated version of a previously relayed and now out-of-date package of knowledge assets to a CSE, and wherein the tracker module is configured to detect modifications of knowledge assets within the package of knowledge assets to be updated and/or modifications of links between knowledge assets within the package of knowledge assets to be updated, executed on the side of the CSE.

8. The computer-implemented knowledge asset distribution platform according to claim 7, wherein the tracker module is configured to prompt the user for confirmation before a knowledge asset with a detected modification is overwritten and/or replaced.

9. The computer-implemented knowledge asset distribution platform according to claim 7, wherein in case a customization and/or a localization of knowledge assets within the package of knowledge assets or of packages of knowledge assets is detected by the tracker module, the customization and/or a localization is at least partly retained after the update.

10. The computer-implemented knowledge asset distribution platform according to claim 1, comprising an interface module, which is configured to allow remote access to packages of knowledge assets distributed by the distribution module, in particular via a web browser, via a web-service or via another distribution method.

11. The computer-implemented knowledge asset distribution platform according to claim 1, with the sender module comprising a consumer import module, which is configured to import a package of knowledge assets to a CSE, thereby integrating the imported package of knowledge assets in an existing set of knowledge assets of the CSE, and with the non-transitory memory unit comprising instructions that, when performed by the processor unit, make the consumer import module:

copy the package of knowledge assets to a database of the CSE, identify all weak links connecting knowledge assets of the package of knowledge assets to be imported with target knowledge assets outside said package of knowledge assets, search at least semi-automatically for knowledge assets in the CSE which correspond to said target knowledge assets, and connect at least a portion of the weak links by establishing strong (intact) links connecting the respective knowledge assets of the package of knowledge assets to said corresponding target knowledge assets.

12. The computer-implemented knowledge asset distribution platform according to claim 11, wherein the consumer import module comprises a linkage unit, which is configured to guide a user in an at least semi-automatic way through a linkage process for a connection and/or a removal of weak links during an import of a package of knowledge assets.

13. The computer-implemented knowledge asset distribution platform according to claim 12, wherein the linkage unit is configured to
search the existing knowledge assets of the CSE
compare at least one characteristic of the existing knowledge assets of the CSE to at least one characteristic of a weak link
create a list of probable target knowledge assets for the weak link on the basis of the existing knowledge assets of the CSE, and
display the list of probable target knowledge assets to a user for selection.

14. The computer-implemented knowledge asset distribution platform according to claim 13, wherein, in case a weak link of a knowledge asset is not re-connected during the import the linkage unit inserts an exceptional value in the knowledge asset, indicating that the connection of the weak link could not be established.

15. The computer-implemented knowledge asset distribution platform according to claim 14, wherein the linkage unit, before inserting the exceptional value in the knowledge asset, reviews an integrity of the knowledge asset by reassessing compliance with at least one integrity constraint.

16. The computer-implemented knowledge asset distribution platform according to claim 15, wherein upon a detection of a violation of an integrity constraint by the linkage unit, the consumer import module transitions from an automatic import mode in an at least semi-automatic import mode and sends out a notification, in particular to a user of the CSE, requesting user guidance, and/or to the browser module.

17. The computer-implemented knowledge asset distribution platform according to claim 16, wherein upon receiving the notification, the browser module initiates a search for at least one knowledge package which is suited for at least partially resolving the violation of the integrity constraint, and wherein the browser module transmits a notification to the user of the CSE suggesting required knowledge packages.

18. The computer-implemented knowledge asset distribution platform according to claim 1, wherein the browser module is configured to create and prepare for display at least one ranked list of related packages of knowledge assets which are to be distributed via the knowledge asset distribution platform, wherein a rank of the ranked list depends on a total number of weak links which are potentially re-connectable by a combination of the package of knowledge assets with the respective related package of knowledge assets.

19. The computer-implemented knowledge asset distribution platform according to claim 1, wherein the browser module is configured to track and prepare for display an origin report of a package of knowledge assets or of a content of the package of knowledge assets and/or of a schema associated with at least one knowledge asset.

20. The computer-implemented knowledge asset distribution platform according to claim 1, wherein the browser module comprises an assessment platform, which is configured to provide at least a validity assessment functionality, an applicability assessment functionality and/or a reputation assessment functionality for the packages for the knowledge assets which are to be distributed, wherein the content of the assessment platform is accessible for users of the knowledge asset distribution platform.

21. The computer-implemented knowledge asset distribution platform according to claim 1, wherein the knowledge assets are bio-medical and/or clinical knowledge assets and wherein the knowledge asset distribution platform is configured to distribute bio-medical and/or clinical knowledge assets.

22. A computer-implemented method for distributing packages of knowledge assets between a plurality of provider system environments (PSE) and/or consumer system environments (CSE), which are adapted to store knowledge assets and to make the knowledge assets available to users of the CSEs via a knowledge asset distribution platform, with at least one processor unit, with at least one non-transitory memory unit, and with a distribution module which is configured to distribute packages of knowledge assets at least by the following steps:
selecting a scope and/or a content of at least one package of knowledge assets which is to be distributed via the knowledge asset distribution platform, from a pool of knowledge assets available within at least one PSE,
receiving packages of knowledge assets to be distributed by the knowledge asset distribution platform from at least one PSE and/or receiving content information of the packages of knowledge assets to be distributed by the knowledge asset distribution platform from the at least one PSE,
storing packages of knowledge assets and/or storing content information on packages of knowledge assets, in particular the packages of knowledge assets and/or the content information received in a previous step, within the non-transitory memory unit,
providing a browser function for browsing the knowledge assets stored within the non-transitory memory and/or for browsing the content information stored within the non-transitory memory for the purpose of finding and/or locating specific packages of knowledge assets and/or for finding and/or locating packages of knowledge assets containing knowledge about specific topics, and
relaying packages of knowledge assets, which have in particular been selected by a user, from the non-transitory memory unit and/or from the at least one PSE to at least one CSE,
wherein
the distribution module comprises a receiver module that comprises an acquisition module, which acquires at least a portion of a set of knowledge assets from the PSE, thereby defining a package of knowledge assets, and wherein
the non-transitory memory unit comprises instructions that, when performed by the processor unit, make the acquisition module:
identify knowledge assets belonging to the portion of knowledge assets which are to be acquired from the PSE by the acquisition module, including at least all links and attributes connected with the knowledge assets of said portion of knowledge assets,
identify all links connecting knowledge assets of said identified portion with knowledge assets of the PSE outside the identified portion of knowledge assets,
create an, in particular virtual, copy of said identified portion of knowledge assets from the PSE, tag the identified links of said, in particular virtual, copy of knowledge assets as weak (at least semi-broken) links, and render the copy of knowledge assets from the PSE, including all strong (intact) links between knowledge assets and including the weak (at least semi-broken) links, available for access via the knowledge asset distribution platform, in particular for a subsequent relaying to a CSE via the sender module.

23. A computer-implemented knowledge asset distribution platform, configured to distribute packages of knowledge assets between a plurality of provider system environments (PSE) and/or consumer system environments (CSE), which are configured to at least store knowledge assets and to make the knowledge assets available to users of the CSE, with at least one processor unit, with at least one non-transitory memory unit, and with a distribution module configured to distribute packages of knowledge assets and comprising:

a receiver module configured to receive packages of knowledge assets, which packages are configured to be distributed by the knowledge asset distribution platform from at least one PSE and/or to receive content information on the packages of knowledge assets to be distributed by the knowledge asset distribution platform from the at least one PSE, a database module configured to store packages of knowledge assets and/or to store content information of or about packages of knowledge assets, in particular the packages of knowledge assets and/or the content information received by the receiver module, within the non-transitory memory unit, a browser module which is configured to provide a browser function for browsing the knowledge assets stored by the database module and/or for browsing and/or finding the content information and/or metadata stored by the database module in order to find and/or locate specific packages of knowledge assets and/or to find and/or locate packages of knowledge assets containing knowledge about specific topics, and a sender module configured to relay packages of knowledge assets, from the non-transitory memory unit and/or from the at least one PSE to at least one CSE, wherein the scope and/or the content of a package of knowledge assets to be distributed via the knowledge asset distribution platform are/is definable by a user of the at least one PSE from a pool of knowledge assets available within the at least one PSE, with the sender module comprising a consumer import module, which is configured to import a package of knowledge assets to a CSE, thereby integrating the imported package of knowledge assets in an existing set of knowledge assets of the CSE, and with the non-transitory memory unit comprising instructions that, when performed by the processor unit, make the consumer import module:

copy the package of knowledge assets to a database of the CSE, identify all weak links connecting knowledge assets of the package of knowledge assets to be imported with target knowledge assets outside said package of knowledge assets, search at least semi-automatically for knowledge assets in the CSE which correspond to said target knowledge assets, and connect at least a portion of the weak links by establishing strong (intact) links connecting the respective knowledge assets of the package of knowledge assets to said corresponding target knowledge assets.

* * * * *